(12) United States Patent
Bryant et al.

(10) Patent No.: US 10,925,654 B2
(45) Date of Patent: Feb. 23, 2021

(54) APPARATUS, SYSTEM, AND METHOD FOR CRIMPING A CABLE FOR BONE FIXATION

(71) Applicant: Cable Fix LLC, Hernando, MS (US)

(72) Inventors: Carey Bryant, Hernando, MS (US); Mark Brinker, Houston, TX (US); William Ricci, Richmond Heights, MO (US); James Duncan, Hernando, MS (US)

(73) Assignee: CABLE FIX LLC, Hernando, MS (US)

( * ) Notice: Subject to any disclaimer, the term of this patent is extended or adjusted under 35 U.S.C. 154(b) by 145 days.

(21) Appl. No.: 16/185,918

(22) Filed: Nov. 9, 2018

(65) Prior Publication Data

US 2019/0083155 A1  Mar. 21, 2019

Related U.S. Application Data

(63) Continuation-in-part of application No. 15/709,436, filed on Sep. 19, 2017, now Pat. No. 10,179,016.

(51) Int. Cl.
| | |
|---|---|
| *A61B 17/88* | (2006.01) |
| *A61B 17/82* | (2006.01) |
| *A61B 90/00* | (2016.01) |
| *A61B 17/68* | (2006.01) |
| *A61B 17/00* | (2006.01) |
| *A61B 17/84* | (2006.01) |

(52) U.S. Cl.
CPC ........ *A61B 17/8861* (2013.01); *A61B 17/683* (2013.01); *A61B 17/82* (2013.01); *A61B 17/8869* (2013.01); *A61B 90/08* (2016.02); *A61B 17/842* (2013.01); *A61B 2017/00367* (2013.01); *A61B 2090/064* (2016.02); *A61B 2090/0807* (2016.02)

(58) Field of Classification Search
CPC ... A61B 17/8861; A61B 17/683; A61B 17/82; A61B 17/8869; A61B 17/842; A61B 90/08; A61B 2090/064; A61B 2090/0807; A61B 2017/00367
USPC .................................. 606/103, 74, 304, 308
See application file for complete search history.

(56) References Cited

U.S. PATENT DOCUMENTS

| | | | |
|---|---|---|---|
| 1,347,579 A | * | 7/1920 | Henrikson ............ B25B 25/005 81/9.3 |
| 2,634,474 A | | 4/1953 | Grayson John |
| 3,952,377 A | | 4/1976 | Morell |
| 4,127,119 A | | 11/1978 | Kronner |
| 4,145,075 A | | 3/1979 | Holzmann |
| 4,250,348 A | | 2/1981 | Kitagawa |
| 4,358,079 A | | 11/1982 | Navarro |
| 4,455,717 A | | 6/1984 | Gray |
| 5,350,204 A | | 9/1994 | Henniger |
| 5,378,027 A | | 1/1995 | Gehring |

(Continued)

*Primary Examiner* — Eduardo C Robert
*Assistant Examiner* — David C Comstock
(74) *Attorney, Agent, or Firm* — Kunzler Bean & Adamson

(57) ABSTRACT

Disclosed herein is a cannulated tool through which a cable is passable. The cannulated tool comprises a body. The cannulated tool also comprises a screw driving feature, rotatable relative to the body. The cannulated tool further comprises an anti-rotation feature, rotatable relative to the screw driving feature. The cannulated tool additionally comprises a cable tensioning feature, configured to tension the cable when passed through the cannulated tool.

14 Claims, 29 Drawing Sheets

(56) References Cited

U.S. PATENT DOCUMENTS

| | | |
|---|---|---|
| 5,383,905 A | 1/1995 | Golds |
| 5,405,172 A | 4/1995 | Mullen, Jr. |
| 5,405,359 A | 4/1995 | Pierce |
| 5,507,754 A | 4/1996 | Green |
| 5,702,397 A | 12/1997 | Goble |
| 5,725,529 A | 3/1998 | Nicholson |
| 5,872,335 A | 2/1999 | Mullen, Jr. |
| 5,908,421 A | 6/1999 | Berger |
| 5,957,953 A | 9/1999 | DiPoto |
| 6,056,773 A | 5/2000 | Bonutti |
| 6,086,608 A | 7/2000 | Ek |
| 6,260,241 B1 | 7/2001 | Brennan |
| 6,306,159 B1 | 10/2001 | Schwartz |
| 6,368,326 B1 | 4/2002 | Dakin |
| 6,488,317 B1 | 12/2002 | Daoud |
| 6,585,730 B1 | 7/2003 | Foerster |
| 6,595,994 B2 * | 7/2003 | Kilpela ............... A61B 17/8861 606/103 |
| 6,648,903 B1 | 11/2003 | Pierson |
| 7,172,595 B1 | 2/2007 | Goble |
| 7,491,217 B1 | 2/2009 | Hendren |
| 7,625,387 B2 | 12/2009 | Wixey |
| 7,674,276 B2 | 3/2010 | Stone |
| 7,717,916 B2 | 5/2010 | Hajianpour |
| 8,419,733 B2 | 4/2013 | Hajianpour |
| 8,469,966 B2 * | 6/2013 | Allen ............... A61B 17/8869 606/103 |
| 9,265,543 B2 | 2/2016 | Gephart |
| 9,375,242 B2 | 6/2016 | Worcel |
| 9,439,698 B2 | 9/2016 | Songer |
| 9,788,875 B2 | 10/2017 | Dell'oca |
| 9,788,877 B2 | 10/2017 | Dell'oca |
| 2001/0008971 A1 | 7/2001 | Schwartz |
| 2001/0025181 A1 | 9/2001 | Freedlan |
| 2002/0116013 A1 | 8/2002 | Gleason |
| 2002/0128684 A1 | 9/2002 | Foerster |
| 2002/0133179 A1 | 9/2002 | McDevitt |
| 2003/0023241 A1 | 1/2003 | Drewry |
| 2003/0225456 A1 | 12/2003 | Ek |
| 2004/0098050 A1 | 5/2004 | Foerster |
| 2004/0127907 A1 | 7/2004 | Dakin |
| 2006/0195104 A1 | 8/2006 | Schlafli |
| 2007/0010817 A1 | 1/2007 | de Conninck |
| 2007/0255317 A1 | 11/2007 | Fanton |
| 2008/0023012 A1 | 1/2008 | Dineen |
| 2008/0147126 A1 | 6/2008 | Tipirneni |
| 2008/0147127 A1 | 6/2008 | Tipirneni |
| 2008/0275469 A1 | 11/2008 | Fanton |
| 2008/0319478 A1 | 12/2008 | Foerster |
| 2009/0131990 A1 | 5/2009 | Tipirneni |
| 2009/0149883 A1 | 6/2009 | Brunsvold |
| 2009/0171357 A1 | 7/2009 | Justin |
| 2009/0248068 A1 | 10/2009 | Lombardo |
| 2009/0254129 A1 | 10/2009 | Tipirneni |
| 2009/0306718 A1 | 12/2009 | Tipirneni |
| 2009/0312794 A1 | 12/2009 | Nason |
| 2010/0049213 A1 | 2/2010 | Serina |
| 2010/0256612 A1 | 10/2010 | Dell'Oca |
| 2010/0292733 A1 | 11/2010 | Hendricksen |
| 2010/0298893 A1 | 11/2010 | Stucki |
| 2010/0312292 A1 | 12/2010 | Tipirneni |
| 2010/0318137 A1 | 12/2010 | Stucki |
| 2011/0034925 A1 | 2/2011 | Tipirneni |
| 2011/0137356 A1 * | 6/2011 | Kollmer ............... A61B 17/683 606/324 |
| 2011/0224676 A1 | 9/2011 | Dell'oca |
| 2011/0295252 A1 | 12/2011 | Tipirneni |
| 2012/0065638 A1 | 3/2012 | Moore |
| 2012/0078300 A1 | 3/2012 | Mayer |
| 2012/0215224 A1 | 8/2012 | Songer |
| 2013/0123841 A1 | 5/2013 | Lyon |
| 2013/0165930 A1 * | 6/2013 | Lehmann ............... A61B 17/88 606/54 |
| 2013/0184708 A1 | 7/2013 | Robinson |
| 2013/0331896 A1 | 12/2013 | Holt |
| 2013/0331897 A1 | 12/2013 | Holt |
| 2014/0025111 A1 | 1/2014 | Bonutti |
| 2014/0107710 A1 | 4/2014 | Forderer |
| 2014/0194907 A1 | 7/2014 | Bonutti |
| 2014/0316461 A1 | 10/2014 | Skiar |
| 2015/0032154 A1 | 1/2015 | Kaplan |
| 2015/0057706 A1 | 2/2015 | Fallin |
| 2015/0073475 A1 | 3/2015 | Schaller |
| 2015/0127003 A1 * | 5/2015 | Songer ............... A61B 17/82 606/74 |
| 2015/0245901 A1 * | 9/2015 | Dougherty ............ A61B 17/0483 606/232 |
| 2016/0038186 A1 | 2/2016 | Herzog |
| 2016/0287248 A1 * | 10/2016 | Levin ............... A61B 17/00234 |
| 2017/0035552 A1 | 2/2017 | Fallin |
| 2017/0065319 A1 | 3/2017 | Oldakowska |
| 2017/0128114 A1 | 5/2017 | Songer |
| 2017/0156738 A1 | 6/2017 | Ricci et al. |
| 2017/0156771 A1 | 6/2017 | Brinker |
| 2017/0156772 A1 | 6/2017 | Brinker et al. |
| 2017/0156774 A1 | 6/2017 | Bryant et al. |
| 2017/0156775 A1 | 6/2017 | Bryant |
| 2017/0156779 A1 | 6/2017 | Bryant |
| 2017/0156847 A1 | 6/2017 | Ricci et al. |
| 2017/0258572 A1 | 9/2017 | Gordon |
| 2017/0265854 A1 | 9/2017 | Heaven |
| 2018/0049735 A1 | 2/2018 | Nguyen |
| 2018/0055550 A1 | 3/2018 | Bryant et al. |
| 2018/0070933 A1 | 3/2018 | Walters |
| 2018/0185080 A1 * | 7/2018 | Bosshard ............ A61B 17/8861 |
| 2019/0183553 A1 * | 6/2019 | Bosshard ............ A61B 17/842 |

\* cited by examiner

APPARATUS, SYSTEM, AND METHOD FOR CRIMPING A CABLE FOR BONE FIXATION

CROSS-REFERENCE TO RELATED APPLICATION

This application is a continuation-in-part of U.S. patent application Ser. No. 15/709,436, filed Sep. 19, 2017, which is incorporated herein by reference.

FIELD

This disclosure relates generally to bone fixation and stabilization techniques and devices, and more particularly to techniques and devices for crimping a cable in a bone fixation and stabilization procedure.

BACKGROUND

Various medical procedures utilize cables to secure damaged skeletal tissue or soft tissue. Tissues, such as bone or soft-tissue, that have been fragmented, fractured, broken, torn, pulled, stretched, or otherwise damaged need to be set and held in specific orientations to properly heal.

Cables may be useful for the purpose of fixating bone fragments in place. For example, cables may encircle or pass through one or more fractured bones. Often, cables are crimped externally to fractured bones to maintain the cables in place relative to the fractured bones. However, for some bones where soft tissue surrounding such bones is minimal, external crimping can cause undesirable and uncomfortable bulges in or displacement of the soft tissue.

SUMMARY

The subject matter of the present application provides embodiments of an apparatus, system, and method that overcome at least some of the above-discussed shortcomings of prior art techniques.

Disclosed herein is a cannulated tool through which a cable is passable. The cannulated tool comprises a body. The cannulated tool also comprises a screw driving feature, rotatable relative to the body. The cannulated tool further comprises an anti-rotation feature, rotatable relative to the screw driving feature. The cannulated tool additionally comprises a cable tensioning feature, configured to tension the cable when passed through the cannulated tool. The preceding subject matter of this paragraph characterizes example 1 of the present disclosure.

The cable tensioning feature comprises an actuator that is rotatable to tension the cable. The preceding subject matter of this paragraph characterizes example 2 of the present disclosure, wherein example 2 also includes the subject matter according to example 1, above.

The cable tool further comprises a tension quick-release mechanism that is selectively operable to release all tension in the cable independently of the cable tensioning feature. The preceding subject matter of this paragraph characterizes example 3 of the present disclosure, wherein example 3 also includes the subject matter according to example 2, above.

The quick-release mechanism comprises a handle that is rotatable to release all tension in the cable. The preceding subject matter of this paragraph characterizes example 4 of the present disclosure, wherein example 4 also includes the subject matter according to example 3, above.

The handle is rotatable, at most, a half turn to release all tension in the cable. The preceding subject matter of this paragraph characterizes example 5 of the present disclosure, wherein example 5 also includes the subject matter according to example 4, above.

The tension quick-release mechanism is integrated into the actuator. The preceding subject matter of this paragraph characterizes example 6 of the present disclosure, wherein example 6 also includes the subject matter according to any one of examples 3-5, above.

The actuator comprises a handle, and the tension quick-release mechanism is integrated into the handle of the actuator. The preceding subject matter of this paragraph characterizes example 7 of the present disclosure, wherein example 7 also includes the subject matter according to example 6, above.

The cannulated tool further comprises a central axis. The screw driving feature comprises a drive gear and a driven gear. The driven gear is rotatable about a first axis that is concentric with the central axis of the cannulated tool. The drive gear is rotatable about a second axis that is oblique to the central axis of the cannulated tool. The preceding subject matter of this paragraph characterizes example 8 of the present disclosure, wherein example 8 also includes the subject matter according to any one of examples 1-7, above.

The second axis is angled at an angle no more than 45-degrees relative to the central axis of the cannulated tool. The preceding subject matter of this paragraph characterizes example 9 of the present disclosure, wherein example 9 also includes the subject matter according to example 8, above.

The cannulated tool further comprises a tension indicator configured to provide a visual indication of a tension force placed on the cable when passed through the cannulated tool and tensioned by the cable tensioning feature. The preceding subject matter of this paragraph characterizes example 10 of the present disclosure, wherein example 10 also includes the subject matter according to any one of examples 1-9, above.

The cannulated tool further comprises a clutch ring. The clutch ring is movable to selectively switch between a tensioning mode, comprising enablement of the cable tensioning feature and disablement of the screw driving feature, and a screw driving mode, comprising enablement of the screw driving feature and disablement of the cable tensioning feature. The preceding subject matter of this paragraph characterizes example 11 of the present disclosure, wherein example 11 also includes the subject matter according to any one of examples 1-10, above, except that in example 11 the screw driving feature is not rotatable relative to the body.

The clutch ring translationally moves along a central axis of the cannulated tool to selectively switch between the tensioning mode and the screw driving mode. The preceding subject matter of this paragraph characterizes example 12 of the present disclosure, wherein example 12 also includes the subject matter according to example 11, above.

Further disclosed herein is a system for crimping a cable. The system comprises a cannulated set screw, comprising a screw channel. The system also comprises a cannulated receptacle, configured to rotatably receive the cannulated set screw and comprising a receptacle channel. The system additionally comprises a cable, positionable in the screw channel of the cannulated set screw and in the receptacle channel of the cannulated receptacle when the cannulated set screw is received by the cannulated receptacle. The system further comprises a cannulated tool configured to prevent rotation of the cannulated receptacle, to tension the cable, and to rotatably drive the cannulated set screw into the cannulated receptacle while the cannulated tool prevents rotation of the cannulated receptacle and tensions the cable.

The preceding subject matter of this paragraph characterizes example 13 of the present disclosure.

The cannulated tool comprises a body. The cannulated tool also comprises a screw driving feature, rotatable relative to the body and configured to co-rotatably engage the cannulated set screw. The cannulated tool additionally comprises an anti-rotation feature, rotatable relative to the screw driving feature and configured to fixedly engage the cannulated receptacle. The cannulated tool further comprises a cable tensioning feature, configured to tension the cable when passed through the cannulated tool. The preceding subject matter of this paragraph characterizes example 14 of the present disclosure, wherein example 14 also includes the subject matter according to example 13, above.

The cable tensioning feature comprises an actuator that is rotatable to tension the cable. The cannulated tool further comprises a tension quick-release mechanism that is selectively operable to release all tension in the cable independently of the cable tensioning feature. The preceding subject matter of this paragraph characterizes example 15 of the present disclosure, wherein example 15 also includes the subject matter according to example 14, above.

The cannulated tool further comprising a central axis. The screw driving feature comprises a drive gear and a driven gear. The driven gear is rotatable about a first axis that is concentric with the central axis of the cannulated tool and concentric with a central axis of the cannulated receptacle when the cannulated tool rotatably drives the cannulated set screw into the cannulated receptacle. The drive gear is rotatable about a second axis that is oblique to the central axis of the cannulated tool and oblique to the central axis of the cannulated receptacle when the cannulated tool rotatably drives the cannulated set screw into the cannulated receptacle. The preceding subject matter of this paragraph characterizes example 16 of the present disclosure, wherein example 16 also includes the subject matter according to any one of examples 14-15, above.

The system further comprises a driving tool configured to rotatably engage the drive gear. A rotational axis of the driving tool is concentric with the second axis and oblique to the first axis when rotatably engaged with the drive gear. The preceding subject matter of this paragraph characterizes example 17 of the present disclosure, wherein example 17 also includes the subject matter according to example 16, above.

The cannulated tool further comprises a clutch ring. The clutch ring is movable to selectively switch between a tensioning mode, comprising enablement of the cable tensioning feature and disablement of the screw driving feature, and a screw driving mode, comprising enablement of the screw driving feature and disablement of the cable tensioning feature. The preceding subject matter of this paragraph characterizes example 18 of the present disclosure, wherein example 18 also includes the subject matter according to any one of examples 14-17, above, except that in example 18 the screw driving feature is not rotatable relative to the body.

The clutch ring translationally moves along a central axis of the cannulated tool to selectively switch between the tensioning mode and the screw driving mode. The preceding subject matter of this paragraph characterizes example 19 of the present disclosure, wherein example 19 also includes the subject matter according to example 18, above.

Additionally disclosed herein is a method of crimping a cable. The method comprises positioning a cable in a screw channel of a cannulated set screw. The method also comprises positioning the cable in a receptacle channel of a cannulated receptacle. The method further comprises with the cable positioned in the screw channel and the receptacle channel, receiving the cannulated set screw in the cannulated receptacle. The method additionally comprises passing the cable through a cannulated tool. The method also comprises tensioning the cable with a cable tensioning feature of the cannulated tool by rotating an actuator of the cannulated tool. The method further comprises engaging the cannulated receptacle with an anti-rotation feature of the cannulated tool. The method additionally comprises after tensioning the cable and engaging the cannulated receptacle with the anti-rotation feature, rotating the cannulated set screw into engagement with the cannulated receptacle by rotating a screw driving feature of the cannulated tool relative to the anti-rotation feature of the cannulated tool. The preceding subject matter of this paragraph characterizes example 20 of the present disclosure.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter, they are not therefore to be considered to be limiting of its scope. The subject matter will be described and explained with additional specificity and detail through the use of the drawings, in which.

DETAILED DESCRIPTION

Figure 1:
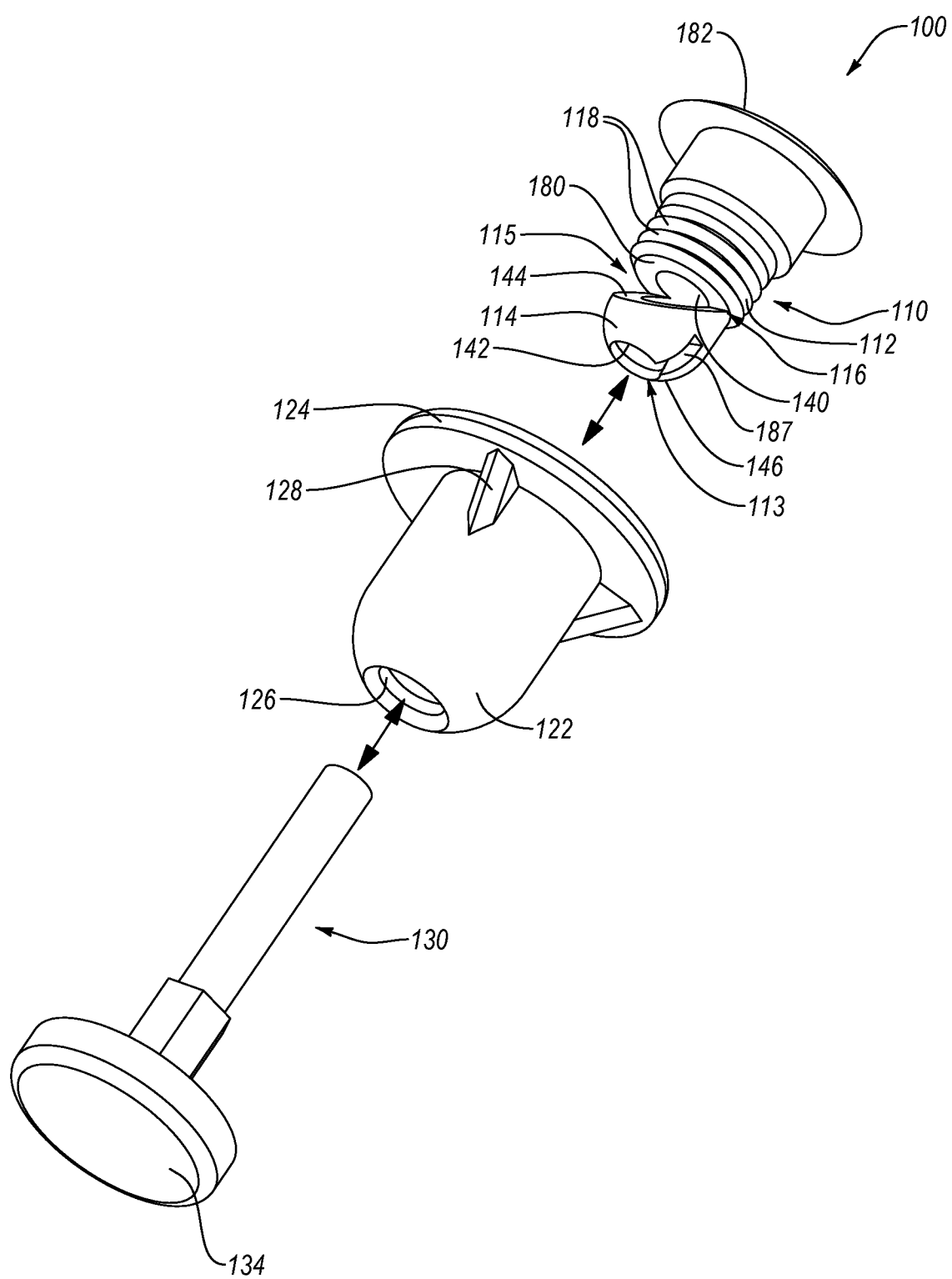
FIG. 1 is an exploded perspective view of an apparatus for crimping a cable, according to one or more examples of the present disclosure.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Referring to FIGS. 1-6, one embodiment of an apparatus 100 for crimping a cable, such as a cable 130, is shown. The apparatus 100 includes a set element 110 and a cannulated receptacle 120 that receives the set element 110. Generally, the apparatus 100 is configured such that as the set element 110 is incrementally received within the cannulated receptacle 120, a portion of the cable 130 in the cannulated receptacle 120 is incrementally bent and correspondingly crimped (see, e.g., FIG. 5). Once the portion of the cable 130 is crimped within the cannulated receptacle 120, the cable 130 is prevented from releasing from the cannulated receptacle 120. Moreover, if the cable 130 is tensioned, crimping the cable 130 maintains the tension in the cable 130. Generally, the cable 130 is crimped when the cable 130 is bent within the cannulated receptacle 120 or otherwise locked within the cannulated receptacle 120. Accordingly, as used herein, crimping can be used interchangeably with locking.

The set element 110 includes a cannulated set screw 112 and a cannulated cable-bending element 113. As defined herein, cannulated means interiorly hollowed or channeled from one end or side to an opposite end or side. In other words, by definition, a cannulated feature is hollow, or has at least one channel, from one end or side of the feature to an opposite end or side of the feature. Consistent with this definition, a cannulated feature has an open-ended channel formed in or extending through the feature. Accordingly, the cannulated set screw 112 has a screw channel 140 and the cannulated cable-bending element 113 has an element channel 142, which is linear. The screw channel 140 and the element channel 142 are concentric in some examples. Moreover, prior to crimping the cable 130, the screw channel 140 is coaxial with a central axis of the cannulated set screw 112 and the element channel 142 is coaxial with a central axis of the cannulated cable-bending element 113. The cross-sectional size and shape of the screw channel 140 and the element channel 142 complements the cross-sectional size and shape of the cable 130. For example, in one implementation, the shape of the screw channel 140 and the element channel 142 is the same as that of the cable 130. However, the size of the screw channel 140 and the element channel 142 is at least as large as (e.g., slightly larger than) that of the cable 130. In this manner, the cable 130 is able to freely enter and pass through the screw channel 140 and the element channel 142.

Figure 13:
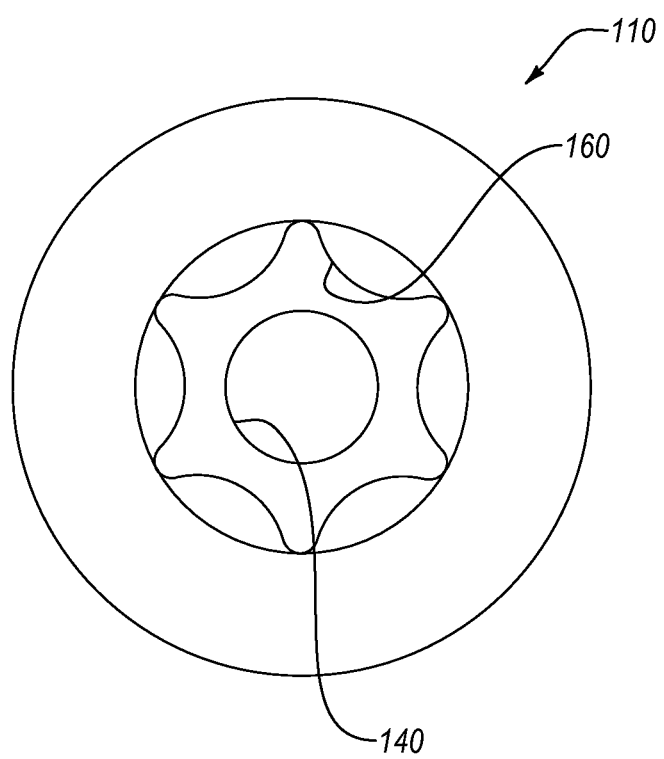
FIG. 13 is a top plan view of a set screw of an apparatus for crimping a cable, according to one or more examples of the present disclosure.

The cannulated set screw 112 has a generally cylindrical shape with a side, having a circular cross-section, extending between two planar ends opposite each other. The two planar ends of the cannulated set screw 112 include an inner end 180 and an outer end 182 (e.g., an exterior-most surface). Furthermore, the cannulated set screw 112 includes external threads 118 extending circumferentially about the side of the cannulated set screw 112. The cannulated set screw 112 further includes a tool recess 160 formed in the outer end 182. The tool recess 160 is concentric with the screw channel 140 in some implementations. As shown in FIG. 13, the tool recess 160 has a non-circular cross-sectional shape along a plane perpendicular to the screw channel 140. For example, in one implementation, the tool recess 160 has a polygonal shape (e.g., hexagonal), ovular shape, or other non-circular shape.

The cannulated cable-bending element 113, which can also be defined as a cable-locking element, is co-movably coupled to the cannulated set screw 112 at a detachment interface 116 (see, e.g., FIG. 1). More specifically, the cannulated cable-bending element 113 includes a first portion 114 co-movably coupled to the inner end 180 of the cannulated set screw 112 at the detachment interface 116. Generally, the detachment interface 116 is defined as an interface configured to allow detachment of the first portion 114 of the cannulated cable-bending element 113 from the cannulated set screw 112 as the cannulated set screw 112 is threadably, or otherwise, incrementally received by the cannulated receptacle 120. The detachment interface 116 is a relatively small area, compared to the overall area of the inner end 180 of the cannulated set screw 112, where the first portion 114 of the cannulated cable-bending element 113 is attached to the inner end 180 of the cannulated set screw 112. In one implementation, the area of the detachment interface 116 is less than 5% of the overall area of the inner end 180.

The detachment interface 116 can be formed and configured in any of various ways that facilitate a secure attachment and co-movability between the first portion 114 of the cannulated cable-bending element 113 and the cannulated set screw 112 before the cannulated set screw 112 is received by the cannulated receptacle 120 and a complete detachment between the first portion 114 of the cannulated cable-bending element 113 and the cannulated set screw 112 after before the cannulated set screw 112 is threadably received by the cannulated receptacle 120. For example, in some implementations, the detachment interface 116 is formed by co-forming the first portion 114 of the cannulated cable-bending element 113 with the cannulated set screw 112 (e.g., to form a one-piece monolithic construction with the cannulated set screw 112), bonding or adhering the first portion 114 of the cannulated cable-bending element 113 to the cannulated set screw 112, welding the first portion 114 of the cannulated cable-bending element 113 to the cannulated set screw 112, or other analogous techniques.

The first portion 114 of the cannulated cable-bending element 113 includes a flat surface 144 that is oblique to the screw channel 140 of the cannulated set screw 112 when the first portion 114 is coupled to the cannulated set screw 112 by the detachment interface 116. As defined herein, the term oblique means non-parallel or not at a 90-degree angle (e.g., greater than 0-degrees and less than 90-degrees or greater than 90-degrees and less than 180-degrees). As will be described in more detail below, after the first portion 114 is decoupled from the set screw 112 along the detachment interface 116, the flat surface 144 may become less oblique to the screw channel 140, such as perpendicular to the screw channel 140. When the first portion 114 is attached to the cannulated set screw 112 by the detachment interface 116, a first notch 115, which, as defined herein, can be a gap or a space, is defined between the inner end 180 of the cannulated set screw 112 and the flat surface 144 of the first portion 114 of the cannulated cable-bending element 113. The first notch 115 has a substantially wedge-shaped cross-section along a plane parallel to the element channel 142. The first portion 114 also has a rounded surface 146, substantially opposite the flat surface 144. Although the rounded surface 146 is curved, the first portion 114 has a generally wedge-shaped cross-section along a plane parallel to the element channel 142.

The cannulated receptacle 120 includes a body 122. In one implementation, the body 122 has a generally cup-shape with a wide outer opening and a narrow inner opening. The cannulated receptacle 120 further includes a receptacle channel 126, which defines the narrow inner opening. The cannulated receptacle 120 also includes an interior cavity 166 defined by an interior surface 127 of the body 122. The interior cavity 166 is sized to allow an entirety of the cannulated cable-bending element 113 to fit within the interior cavity 166. Formed into the interior surface 127 of the body 122 at the wide outer opening are internal threads 162. The internal threads 162 are configured to threadably engage the external threads 118 of the cannulated set screw 112. Although not shown, it is recognized that in some implementations the relative location of the external threads 118 and the internal threads 162 may be reversed (e.g., the cannulated set screw 112 could have internal threads and the cannulated receptacle 120 could have external threads). The interior surface 127 at the narrow inner opening or receptacle channel 126 is curved or rounded to complement the rounded surface 146 of the first portion 114 in some implementations. For example, the rounded surface 146 of the first portion 114 is convex and the interior surface 127 at the narrow inner opening is concave. The internal threads 162 and external threads 118 are concentric with the cable 130 when the cable 130 passes through the apparatus 100. Although a threaded engagement between the cannulated set screw and the cannulated receptacle is shown, any of various other engagements can be used to facilitate translational movement of the cannulated set screw within the cannulated receptacle and detachment of the cable-bending element 113 from the cannulated set screw 112.

Additionally, in some implementations, the cannulated receptacle 120 includes a lip 124 protruding outwardly from the body 122 at the wide outer opening. According to one example, the lip 124 has an annular shape and an outer circumference that is greater than an outer circumference of the body 122. In some examples, a footprint of the lip 124 in plan is greater than that of the body 122.

According to certain examples, the cannulated receptacle 120 also includes one or more fins 128 protruding outwardly from the body 122 between the lip 124 and the receptacle channel 126. In one implementation, each fin 128 has a sharp outward edge. The body 122, the lip 124, and the fins 128 may be co-formed together such that the cannulated receptacle 120 has a one-piece monolithic construction.

Figure 3:
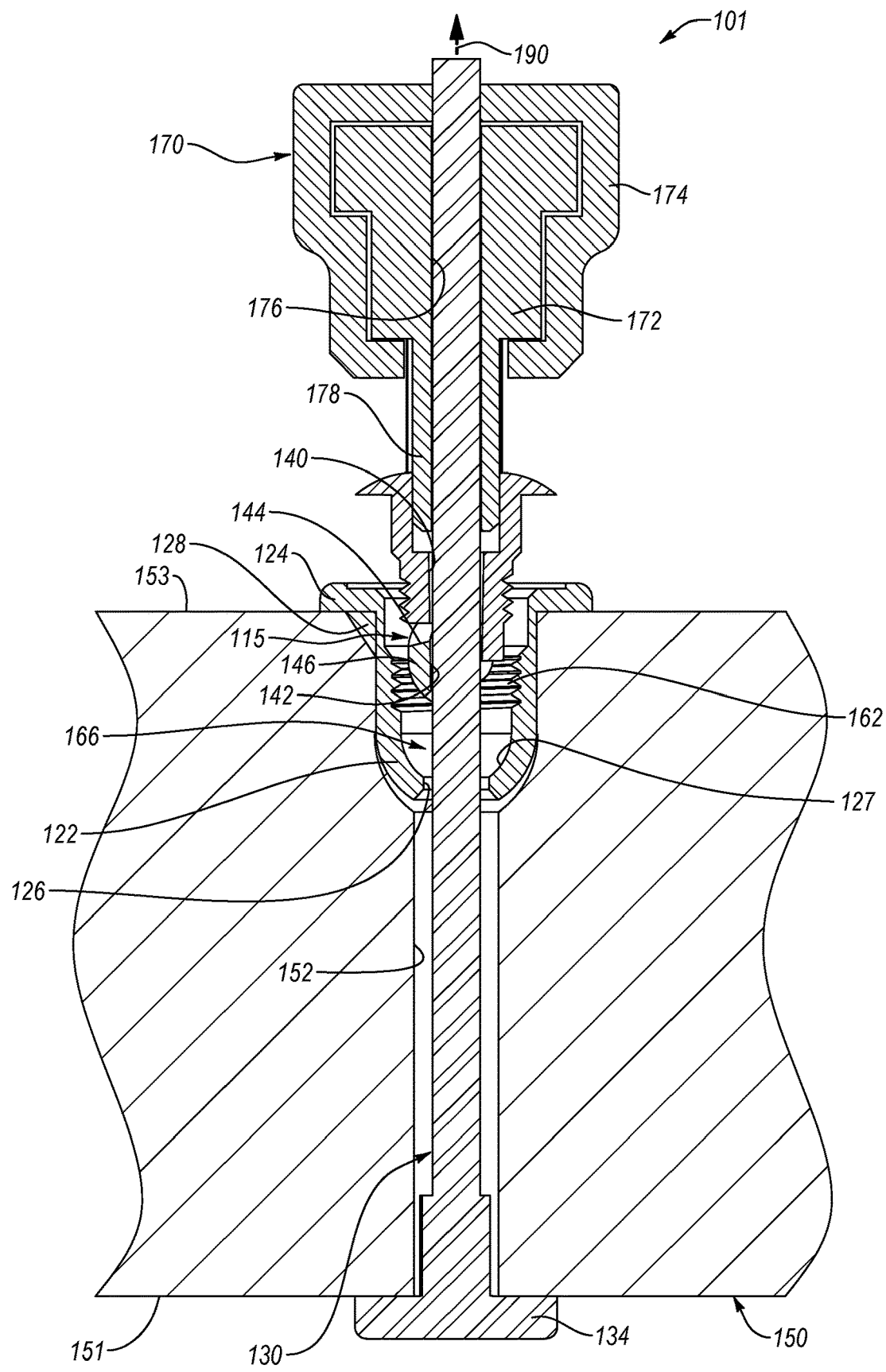
FIG. 3 is a cross-sectional side elevation view of the apparatus of FIG. 1, shown partially embedded in a bone and with the set element of the apparatus in a partially inserted position, according to one or more examples of the present disclosure.

Referring to FIG. 3, the apparatus 100 can form part of a system 101 for crimping a cable. The system 101 includes the apparatus 100, the cable 130, and a cannulated tool 170. According to one example, the cable 130 is utilized in a procedure for reducing and stabilizing fractures in bone and/or subluxations or dislocations of joints. The cable 130 can be any of various flexible cord-like elements, such as a wires, filaments, weaves, or threads, whether bundled or individual. The cable 130 may be made from any one of various materials. For example, in specific implementations, the cable 130 is made from metal, such as stainless steel, titanium, or any other metal.

In some implementations, the cable 130 is capable of holding a measurable and adjustable tension and causing a measurable and adjustable compression of bone (e.g., compressing together fragments of the same bone or compressing together different bones). In other words, the tension in the cable 130 can be measured, such as by a tension measuring device, and can be adjusted, such as after an initial tensioning of the cable 130. In one embodiment, the measurable and adjustable tension may be a specific, known, predictable, expected, controllable, anticipated, desired, repeatable, sustainable, and/or pre-determinable tension. For example, the cable 130 may be tensioned to a measurable and adjustable tension in order to facilitate the reduction and fixation of fractures or to otherwise facilitate the repair of joint dislocations or soft-tissue damage. In other words, in certain implementations, the cable 130 is not a conventional suture or conventional thread material, since such materials are incapable of, or at least not well-suited for, maintaining a measurable and adjustable tension. Thus, in some implementations, the cable 130 can be a flexible, yet substantially non-stretchable, elongate cord-like element that can be tensioned to a measurable and adjustable tension. In such implementations, because the cable 130 is capable of maintaining or retaining a measurable and adjustable tension, the effectiveness and reproducibility of successful surgical procedures is improved. In other words, different surgical procedures relating to different tissues (e.g., bones) in the body may involve different degrees of retention/fixation force (e.g., the fixation force required to reduce a fracture in the femur may be greater than the fixation force required to reduce a fracture in the patella). Accordingly, the ability of the cable 130 to be tensioned to a measurable and adjustable tension improves the reliability and reproducibility of surgical procedures when compared with other medical procedures that do not utilize cables.

A stop 134 is non-movably fixed to a first end of the cable 130. As defined herein, the stop 134 can be any of various features, such as nuts, clips, conventional washers, pins, balls, caps, lids, or the like, that are attachable to the first end of the cable 130 and capable of engaging an opening (e.g., a surface adjacent to or defining the opening) to prevent further passage of the cable 130 through the opening. In one embodiment, the stop 134 resembles a flange or conventional washer. The stop 134 can be integrated into or permanently attached to the first end of the cable 130. For example, the stop 134 may be swaged, crimped, welded, bonded, or otherwise fixedly secured to the cable 130. In another embodiment, the stop 134 can be detachably coupled to the cable 130, thus allowing for stops with different shapes, dimensions, angles, etc. to be alternatively coupled to the same cable as desired.

As shown in FIG. 3, the cannulated tool 170 includes a tool channel 176 extending an entire length of the cannulated tool 170. The cannulated tool 170 is positionable relative to the apparatus 100 such that the tool channel 176 is concentric with the screw channel 140 of the cannulated screw 112 and the element channel 142 of the cannulated cable-bending element 113. Moreover, the tool channel 176 is coaxial with a central axis of the cannulated tool 170. However, in other embodiments, the tool channel 176, or at least a portion of the tool channel 176, is not coaxial with the central axis of the cannulated tool 170 and not concentric with the screw channel 140 of the cannulated screw 112 and the element channel 142 of the cannulated cable-bending element 113. The cross-sectional size and shape of the tool channel 176 complements the cross-sectional size and shape of the cable 130. For example, in one implementation, the shape of the tool channel 176 is the same as that of the cable 130. However, the size of the tool channel 176 is at least as large as (e.g., slightly larger than) that of the cable 130. In this manner, the cable 130 is able to freely enter and pass through the tool channel 176.

The cannulated tool 170 also includes a screw driving portion 172 and a tensioning portion 174. Generally, the screw driving portion 172 is configured to rotate the cannulated set screw 112 relative to the cannulated receptacle 120 for threadably coupling the cannulated set screw 112 to the cannulated receptacle 120. The screw driving portion 172 includes a screw engagement end 178 that is configured to engage the tool recess 160. For example, the screw engagement end 178 may have a male portion shaped and sized to be inserted into and matingly engage the tool recess 160. When engaged, rotation of the screw engagement end 178 rotates the tool recess 160 and thus the cannulated set screw 112. The tool channel 176 allows the screw driving portion 172 to rotate around the cable 130 without rotating the cable 130. The screw engagement end 178 of the cannulated tool 170 may also have a skirt that surrounds the cannulated set screw 112 when the screw engagement end 178 is engaged with the tool recess 160. The length of the skirt relative to the length of the male portion of the screw engagement end 178 may be preselected to ensure the cannulated set screw 112 is properly inserted into the cannulated receptacle 120 to a desired depth and to prevent over-rotating or over-torquing of the cannulated set screw 112.

The tensioning portion 174 of the cannulated tool 170 is configured to pull the cable 130 in the direction indicated by the directional arrow 190 in FIG. 3. With the first end of the cable 130 fixed (e.g., the stop 134 abuts an object, such as bone 150), pulling the cable 130 generates tension in the cable 130. The force of the pulling on the cable 130 by the tensioning portion 174, and thus the amount of tension in the cable 130, can be selectable and measurable. Moreover, the tensioning portion 174 is configured to maintain the tension in the cable 130 as the cannulated set screw 112 is threadably engaged with the cannulated receptacle 120. For example, in one implementation, the screw driving portion 172 of the cannulated tool 170 can be rotatable relative to the tensioning portion 174 of the cannulated tool 170.

According to one particular example, the system 101 is used in a bone fixation procedure for fixating a bone, such as the bone 150. Although the bone 150 is shown as a single, non-fractured, bone, the bone 150 may be separated into two portions by a fracture, or the bone 150 may be two different bones fixated or stabilized relative to each other. The bone fixation procedure includes forming a through-hole 152 in the bone 150. The through-hole 152 extends from a first open end at a first surface 151 of the bone 150 to a second open end at a second surface 153 of the bone 150. The cross-sectional size and shape of the through-hole 152 complements the cross-sectional size and shape of the cable 130. For example, in one implementation, the shape of the through-hole 152 is the same as that of the cable 130. However, the size of the through-hole 152 is at least as large as (e.g., slightly larger than) that of the cable 130. In this manner, the cable 130 is able to freely enter and pass through the through-hole 152. However, the through-hole 152 is smaller than the stop 134 such that the stop 134 is capable of abutting the first surface 151 of the bone 150 to prevent the cable 130 from passing entirely through the through-hole 152.

At the second surface 153 of the bone 150, which can be any of various tissues, including bone, the through-hole 152 includes a counterbore 154 with a cross-sectional area larger than that of the through-hole 152 at the first surface 151. Generally, the counterbore 154 is sized to nestably receive the body 122 of the cannulated receptacle 120. Accordingly, the counterbore 154 may have a size and shape that complements the size and shape of the body 122 of the cannulated receptacle 120. The through-hole 152 can be formed using any of various hole-forming techniques.

The bone fixation and/or tissue stabilization procedure disclosed herein includes nestably inserting the body 122 of the cannulated receptacle 120 into the counterbore 154 until the lip 124 rests on the second surface 153 of the bone 150. The lip 124 helps to keep the cannulated receptacle 120 at the second surface 153, by preventing the cannulated receptacle 120 from penetrating through the bone toward the first surface 151, as the cable 130 is tensioned. Additionally, as the cannulated receptacle 120 is nestably inserted into the counterbore 154, the fins 128 penetrate or embed into the bone 150 around the counterbore 154. When embedded into the bone 150, the fins 128 help to prevent rotation of the cannulated receptacle 120 relative to the bone 150 as the cannulated set screw 112 is rotated relative to the cannulated receptacle 120.

Before or after the cannulated receptacle 120 is inserted into the counterbore 154, the set element 110 is initially inserted into the cannulated receptacle 120 such that the cannulated cable-bending element 113 is within the interior cavity 166. For example, the cannulated set screw 112 can be only partially threadably engaged with the cannulated receptacle 120, such as shown in FIGS. 2 and 3.

Before or after the set element 110 is initially inserted into the cannulated receptacle 120, the cable 130 is inserted into the through-hole 152 at the first surface 151 and passed through the through-hole 152 until part of the cable 130 extends out of the through-hole 152 at the second surface 153. In one implementation, the cannulated receptacle 120, is inserted into the counterbore 154 before the cable 130 is passed through the through-hole 152, such that the cable 130 passes through the receptacle channel 126 of the cannulated receptacle 120 while in the counterbore 154. According to one implementation, the set element 110 also is initially inserted into the cannulated receptacle 120 before the cable 130 is passed through the through-hole 152, such that the cable 130 passes through the receptacle channel 126 of the cannulated receptacle 120, the element channel 142 of the cannulated cable-bending element 113, and the screw channel 140 of the cannulated set screw 112 while the cannulated receptacle 120 is in the counterbore 154 and the set element 110 is partially in the cannulated receptacle 120. In yet another implementation, the cable 130 is passed through the through-hole 152 first and then the cannulated receptacle 120 before the cannulated receptacle 120 is inserted into the counterbore 154 and the set element 110 before or after being received by the cannulated receptacle 120.

Figure 2:
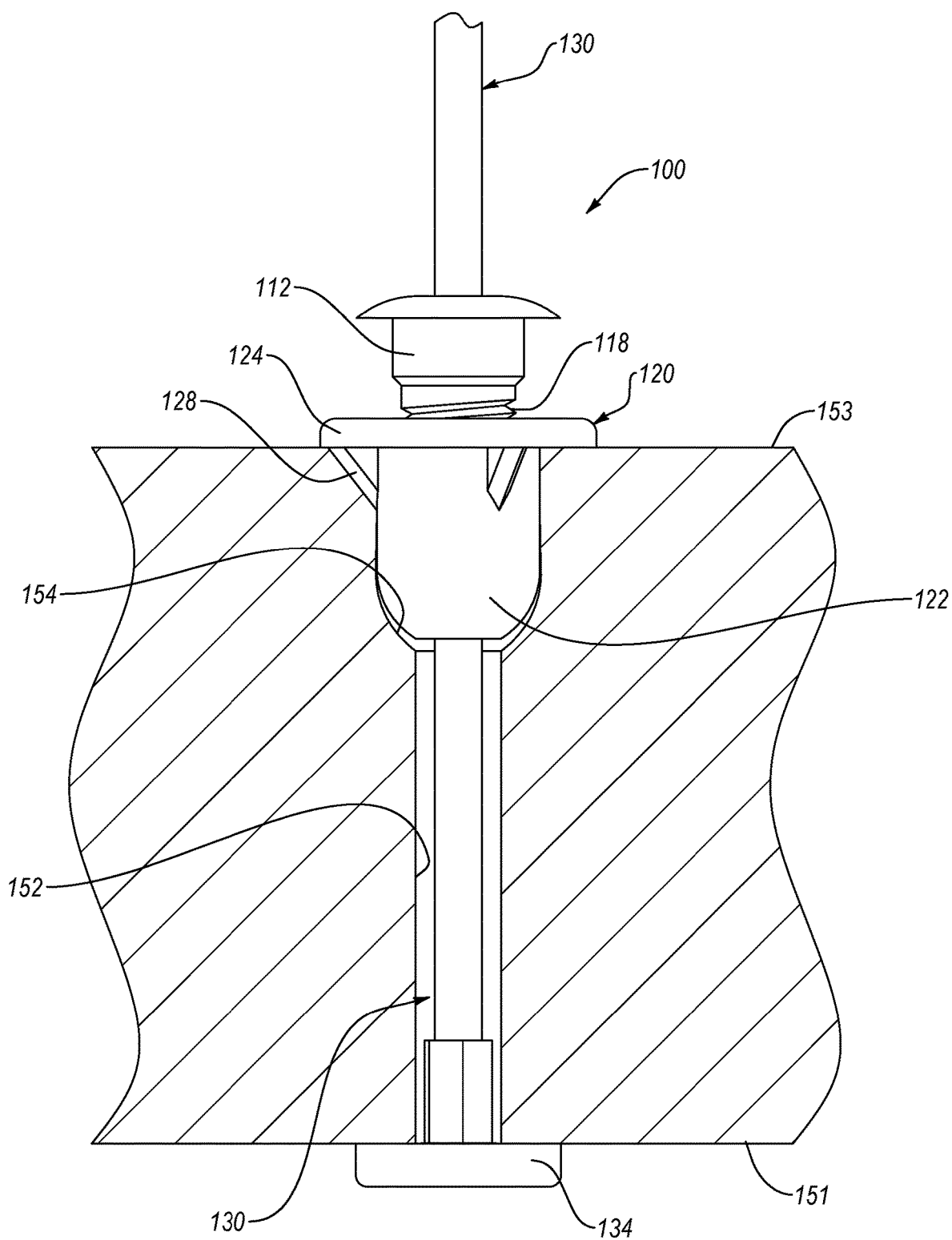
FIG. 2 is a partial cross-sectional side elevation view of the apparatus of FIG. 1, shown partially embedded in a bone and with a set element of the apparatus in a partially inserted position, according to one or more examples of the present disclosure.

With the cannulated receptacle 120 inserted into the counterbore 154, the set element 110 partially received by the cannulated receptacle 120, and the cable 130 positioned in the through-hole 152, cannulated receptacle 120, and the set element 110 as shown in FIGS. 2 and 3, the cannulated tool 170 can be placed around the cable 130 exiting from the second surface 153 of the bone and the cannulated set screw 112. First, the cannulated tool 170 is used to tension the cable 130 to a measurable and adjustable tension. Then, with the cable 130 in tension, the cannulated tool 170 is used to further threadably insert the set element 110 into the cannulated receptacle 120 by rotating the cannulated set screw 112 relative to the cannulated receptacle 120.

As the set element 110 is rotated, a resistance to rotation of the first portion 114 of the cable-bending element 113 relative to the cannulated set screw 112 generates a shear force on the detachment interface 116. When the shear force exceeds the shear strength of the detachment interface 116, the first portion 114 shears away from the cannulated set screw 112 at the detachment interface 116. In one implementation, the area of the detachment interface 116 is small enough to give the detachment interface 116 a shear strength low enough such that within a first full rotation of the cannulated set screw 112 relative to the cannulated receptacle 120 results in the first portion 114 shearing away from the cannulated set screw 112. In other implementations, the area of the detachment interface 116 is small enough to give the detachment interface 116 a shear strength low enough such that within a second, third, or higher rotation of the cannulated set screw 112 relative to the cannulated receptacle 120 results in the first portion 114 shearing away from the cannulated set screw 112.

After the first portion 114 shears away from the cannulated set screw 112, because the first portion 114 is able to rotate relative to the cannulated set screw 112, further insertion of the cannulated set screw 112 into the cannulated receptacle 120 causes the inner end 180 of the cannulated set screw 112 to engage the flat surface 144 of the first portion 114. As indicated by a directional arrow in FIG. 6, engagement between the inner end 180 of the cannulated set screw 112 and the flat surface 144 of the first portion 114 causes the first portion 114 to rotate within the interior cavity 166 of the cannulated receptacle 120 about an axis perpendicular to the cable 130. Rotation of the first portion 114 in this manner correspondingly closes the first notch 115 and rotates the element channel 142 of the first portion 114. In some implementations, as shown in FIG. 1, the first portion 114 includes a slot 187 configured to receive a portion of the cable 130 as the first portion 114 rotates, which facilitates further rotation of the first portion 114 about the axis perpendicular to the cable 130.

As the first portion 114 rotates about the axis perpendicular to the cable 130, the element channel 142 engages the portion of the cable 130 within the element channel 142 and forces this portion of the cable 130 to corresponding rotate relative to adjacent portions of the cable 130. Rotation of the portion of the cable 130 within the element channel 142 causes the adjacent portions of the cable 130 to bend or deform to form a bend 192 or crimp in the cable 130. In one implementation, the rounded surface 146 of the first portion 114 of the cannulated cable-bending element 113 engages a rounded portion of the interior surface 127 of the body 122 of the cannulated receptacle 120 to aid in rotating the first portion 114 within the interior cavity 166.

Figure 4:
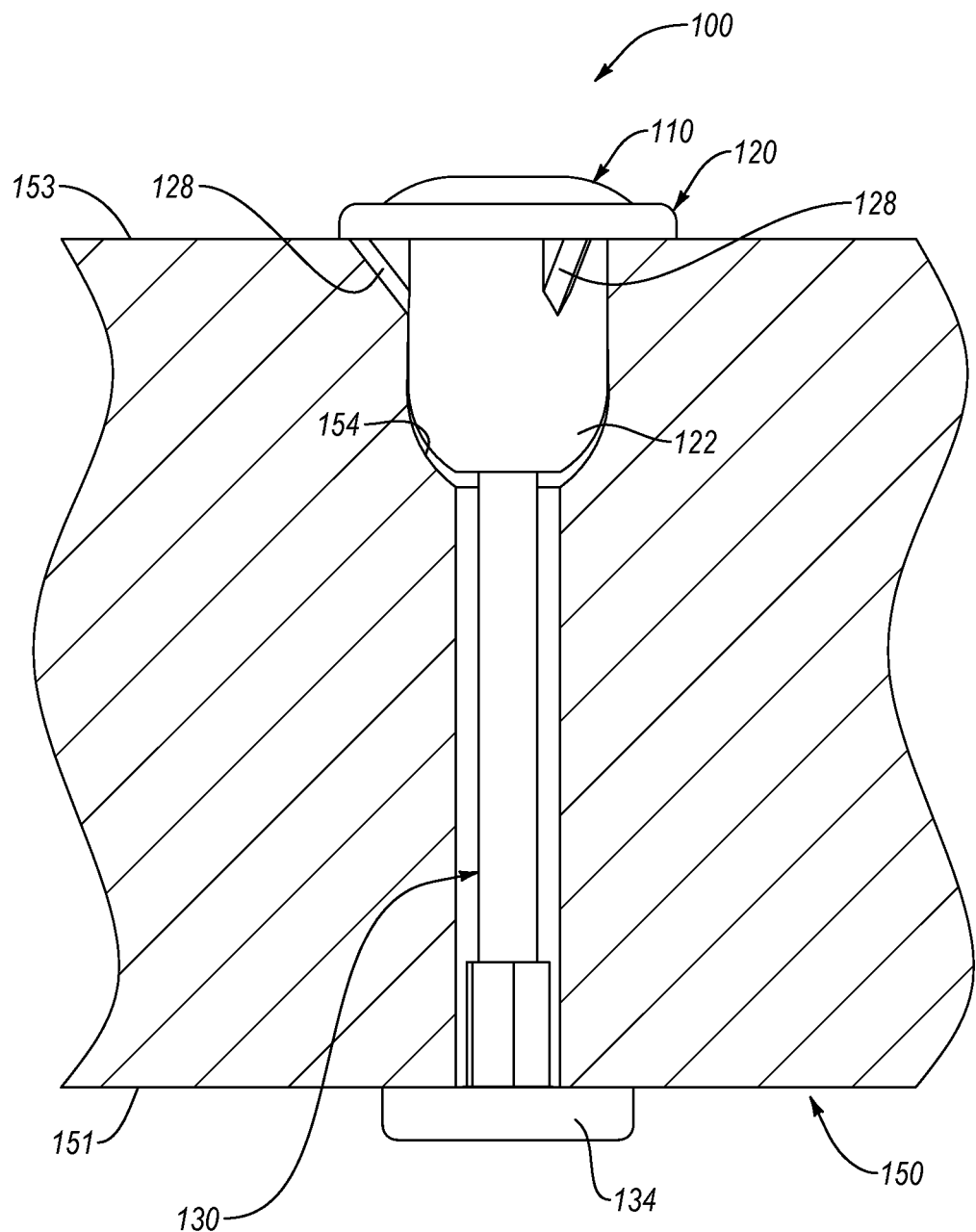
FIG. 4 is a partial cross-sectional side elevation view of the apparatus of FIG. 1, shown partially embedded in a bone and with the set element of the apparatus in a fully inserted position, according to one or more examples of the present disclosure.
Figure 5:
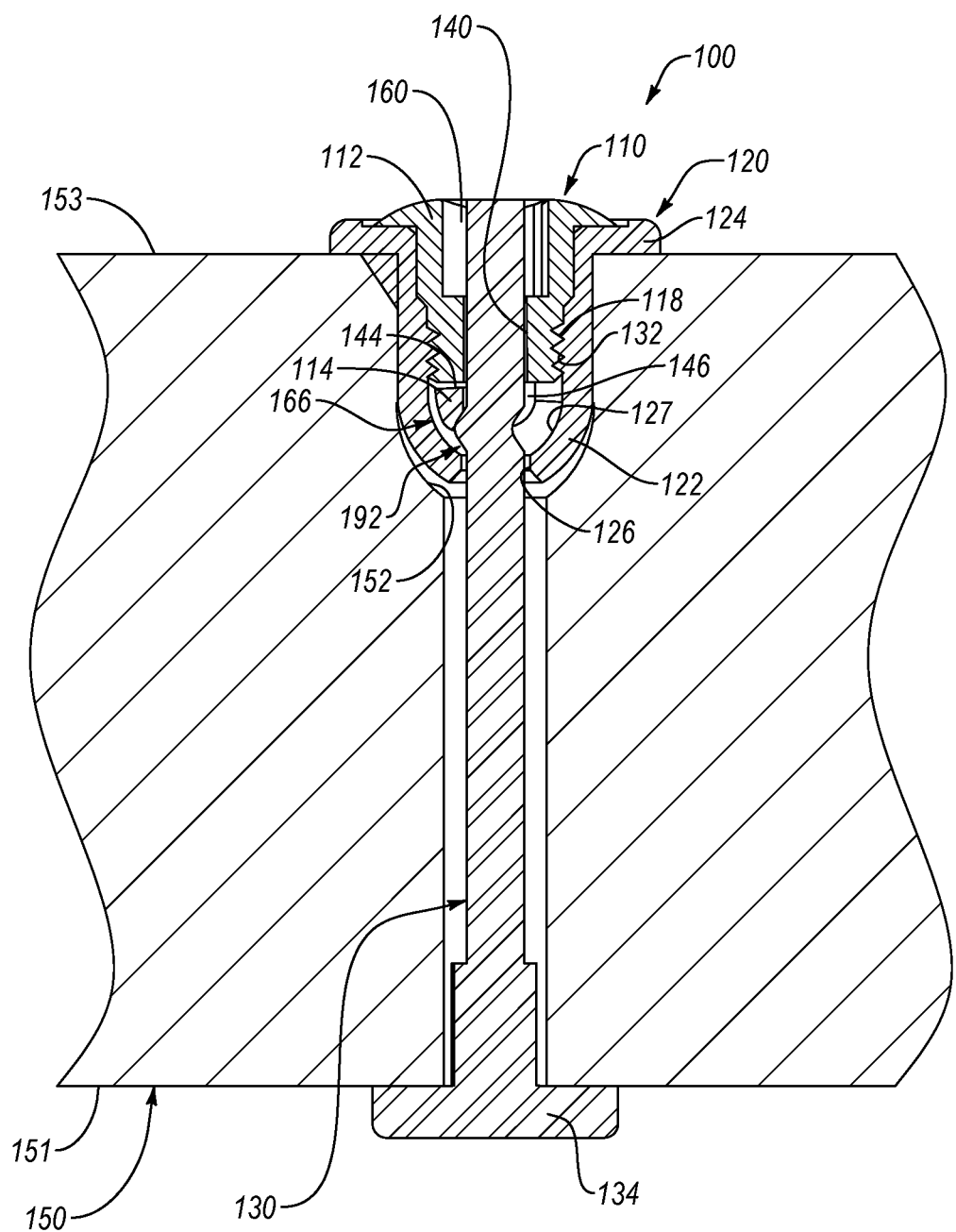
FIG. 5 is a cross-sectional side elevation view of the apparatus of FIG. 1, shown partially embedded in a bone and with the set element of the apparatus in a fully inserted position, according to one or more examples of the present disclosure.
Figure 6:
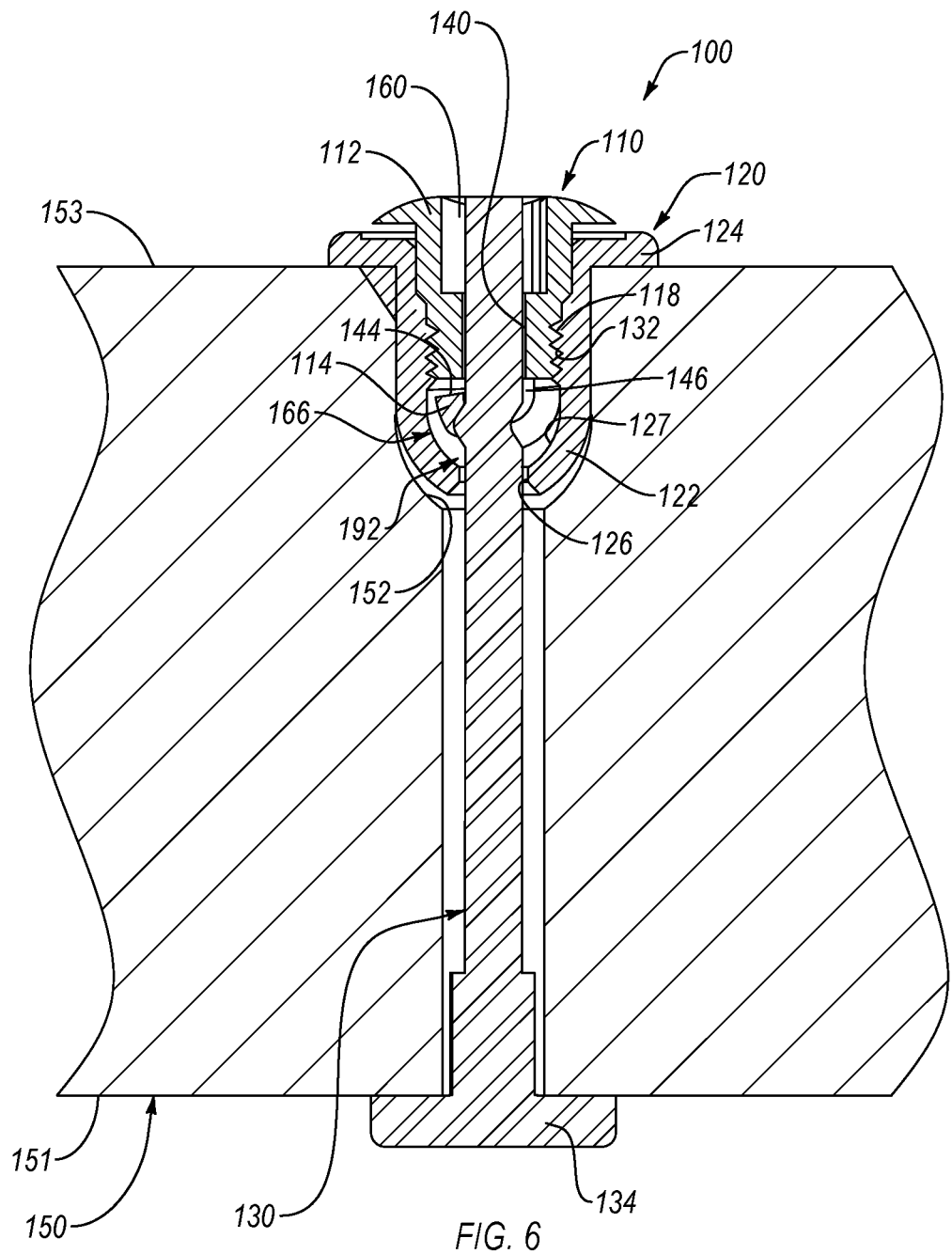
FIG. 6 is a cross-sectional side elevation view of the apparatus of FIG. 1, shown partially embedded in a bone and with the set element of the apparatus in a partially inserted position, according to one or more examples of the present disclosure.
Figure 7:
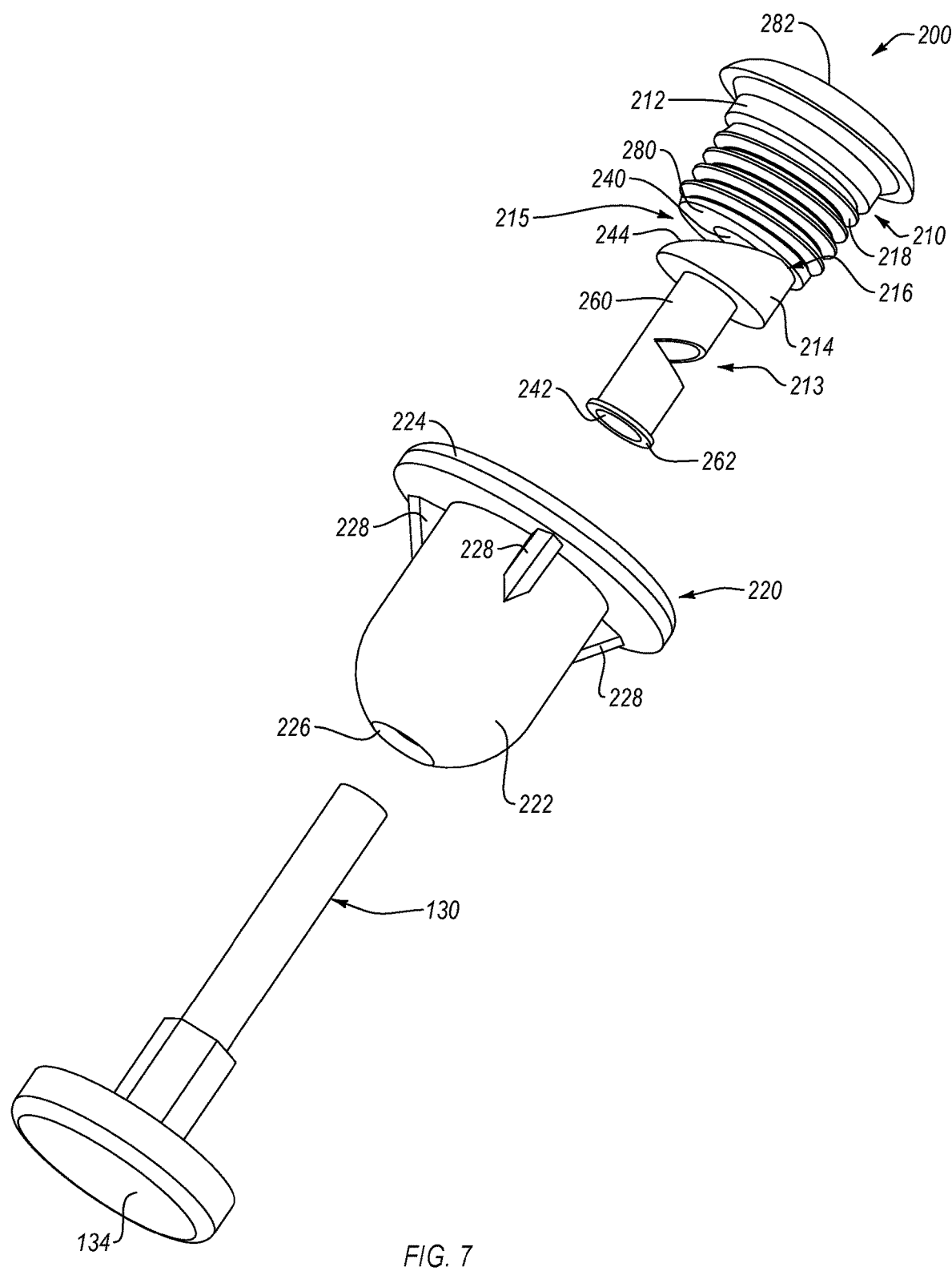
FIG. 7 is an exploded perspective view of an apparatus for crimping a cable, according to one or more examples of the present disclosure.
Figure 8:
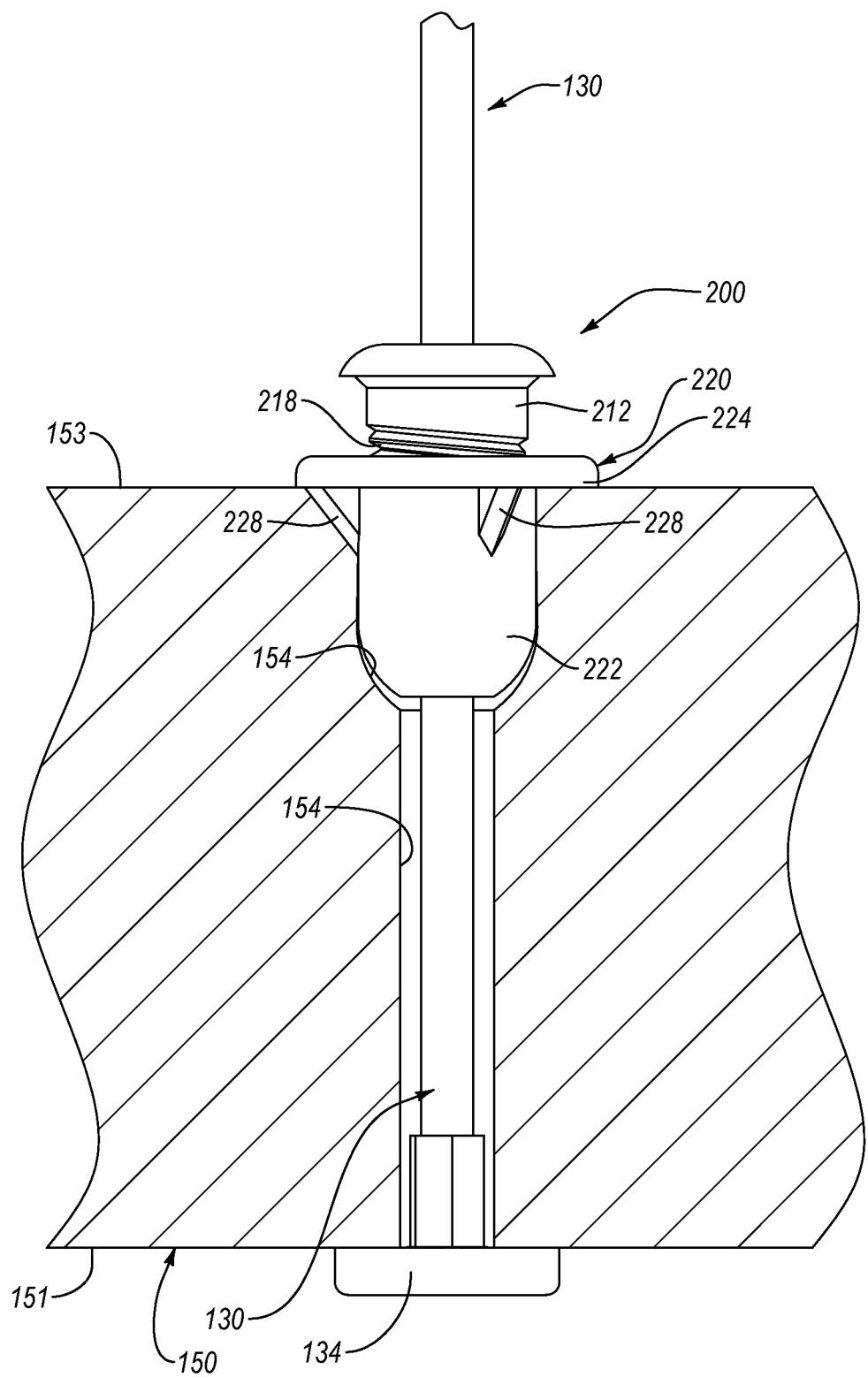
FIG. 8 is a partial cross-sectional side elevation view of the apparatus of FIG. 7, shown partially embedded in a bone and with a set element of the apparatus in a partially inserted position, according to one or more examples of the present disclosure.
Figure 9:
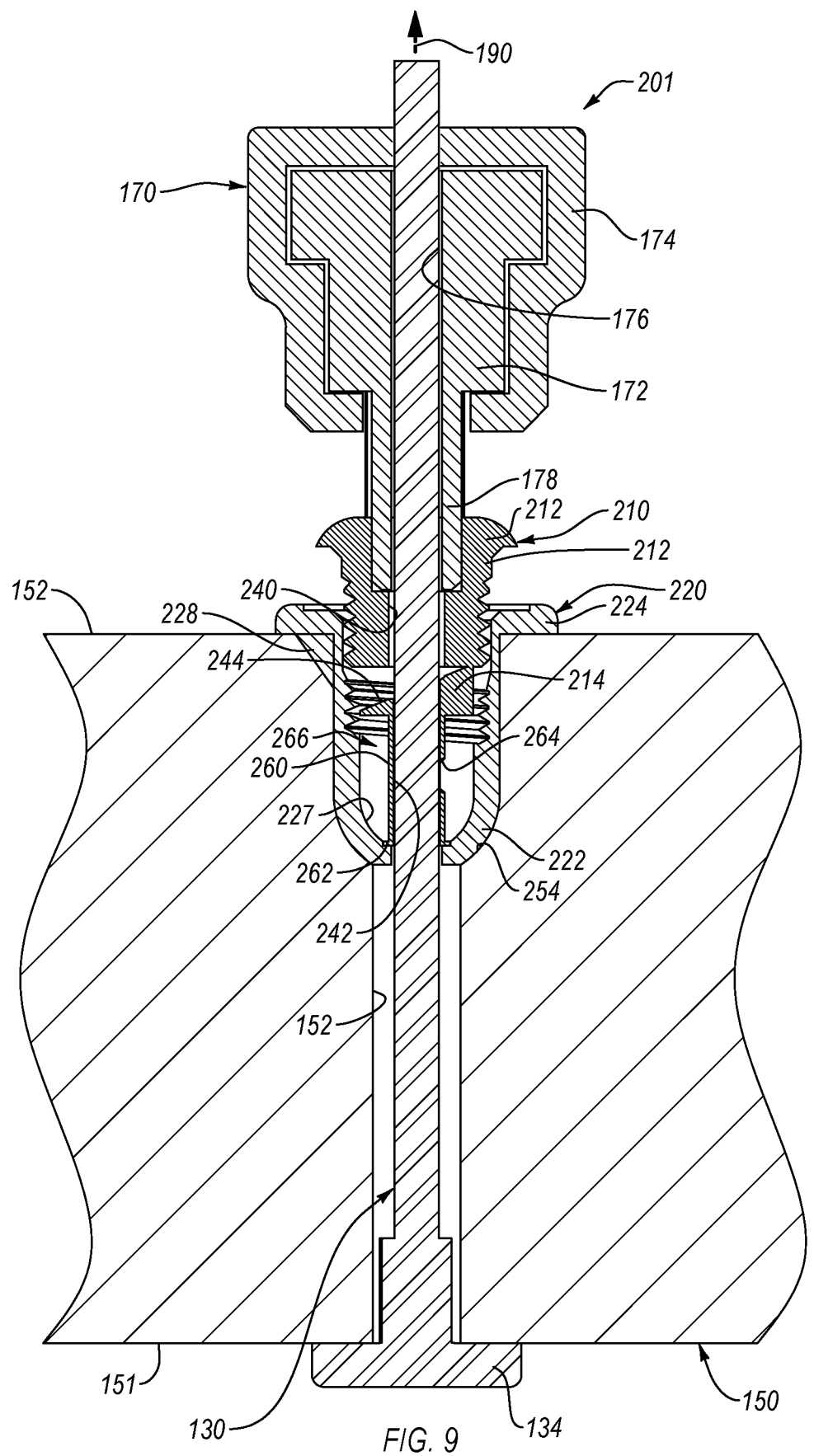
FIG. 9 is a cross-sectional side elevation view of the apparatus of FIG. 7, shown partially embedded in a bone and with the set element of the apparatus in a partially inserted position, according to one or more examples of the present disclosure.
Figure 10:
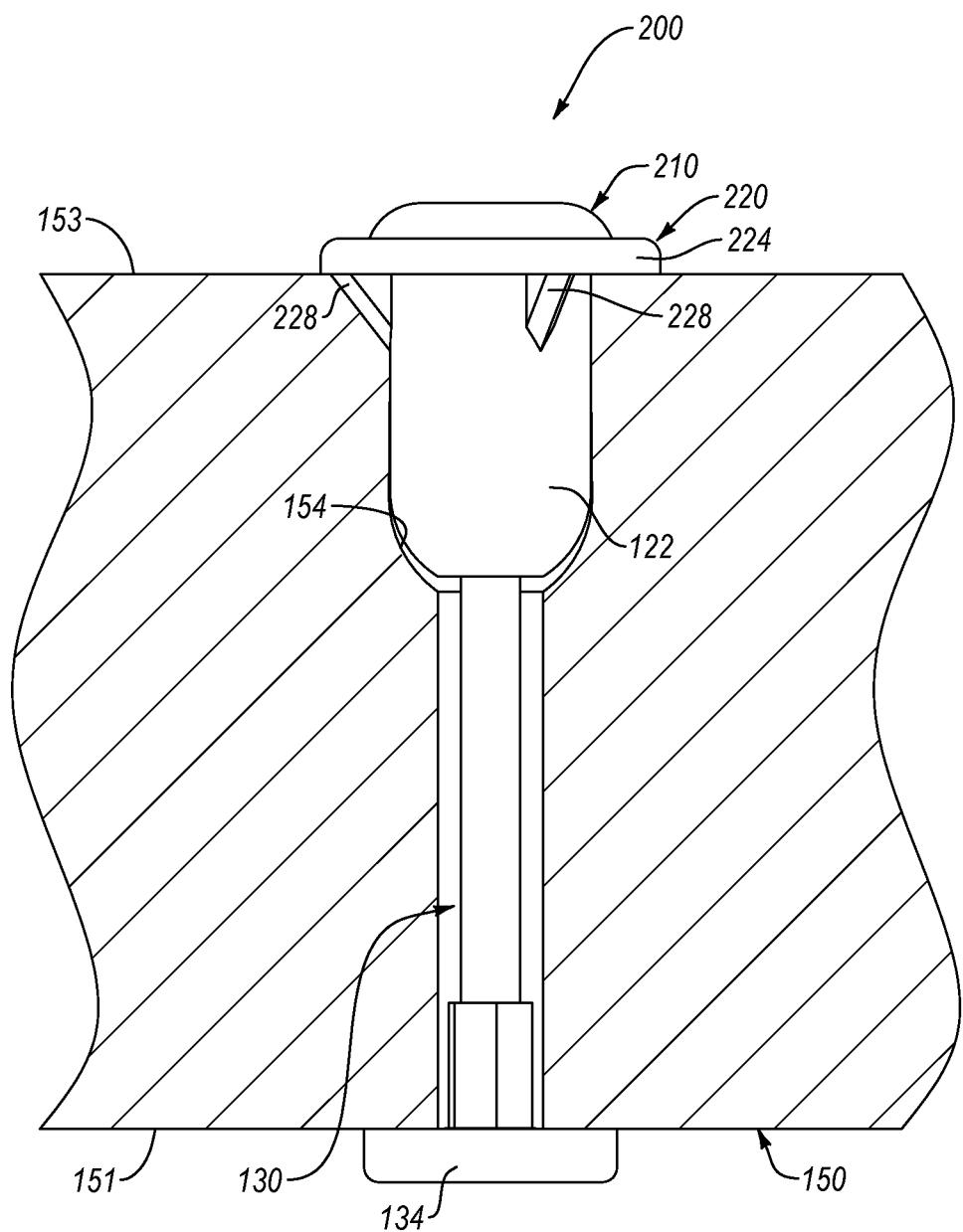
FIG. 10 is a partial cross-sectional side elevation view of the apparatus of FIG. 7, shown partially embedded in a bone and with the set element of the apparatus in a fully inserted position, according to one or more examples of the present disclosure.

Further insertion of the cannulated set screw 112 causes further bending of the cable 130, which continues until the cannulated set screw 112 is fully inserted into the cannulated receptacle 120 as shown in FIGS. 4 and 5. In one implementation, the cannulated set screw 112 is fully inserted into the cannulated receptacle 120 when the outer end 182 of the cannulated set screw 112 is flush with an exterior-most surface of the lip 124 of the cannulated receptacle 120. At full insertion of the cannulated set screw 112 into the cannulated receptacle 120, the cable 130 is sufficiently bent that the bends formed in the cable 130 prevent the cable 130 from sliding through the element channel 142. In this manner, the cable 130 is crimped within the cannulated receptacle 120, which is within an interior of the bone 150, to prevent movement of the cable 130 relative to the apparatus 100 and the bone 150 and maintain any tension in the cable 130. Accordingly, the actual bend 192 crimp in the cable 130 is located within an interior of the bone 150. The cable 130, after being crimped, can then be cut to remove excess portions of the cable 130 extending from the apparatus 100. For example, as shown in FIG. 5, the cable 130 can be cut flush with the outer end 182 of the cannulated set screw 112 and an outer end of the cannulated receptacle 120. Accordingly, apparatus 100 is configured to keep portions of the apparatus 100 and cable 130 protruding exteriorly of the bone 150 to a minimum. In other words, the apparatus 100 promotes internal crimping (e.g., crimping internal to the bone or within an interior of the bone such that the cable is crimped at a location within an interior of the bone), which helps to reduce bulging and displacement of soft tissue around bones where soft tissue surrounding such bones is minimal, such as around ankle bones.

Figure 14:
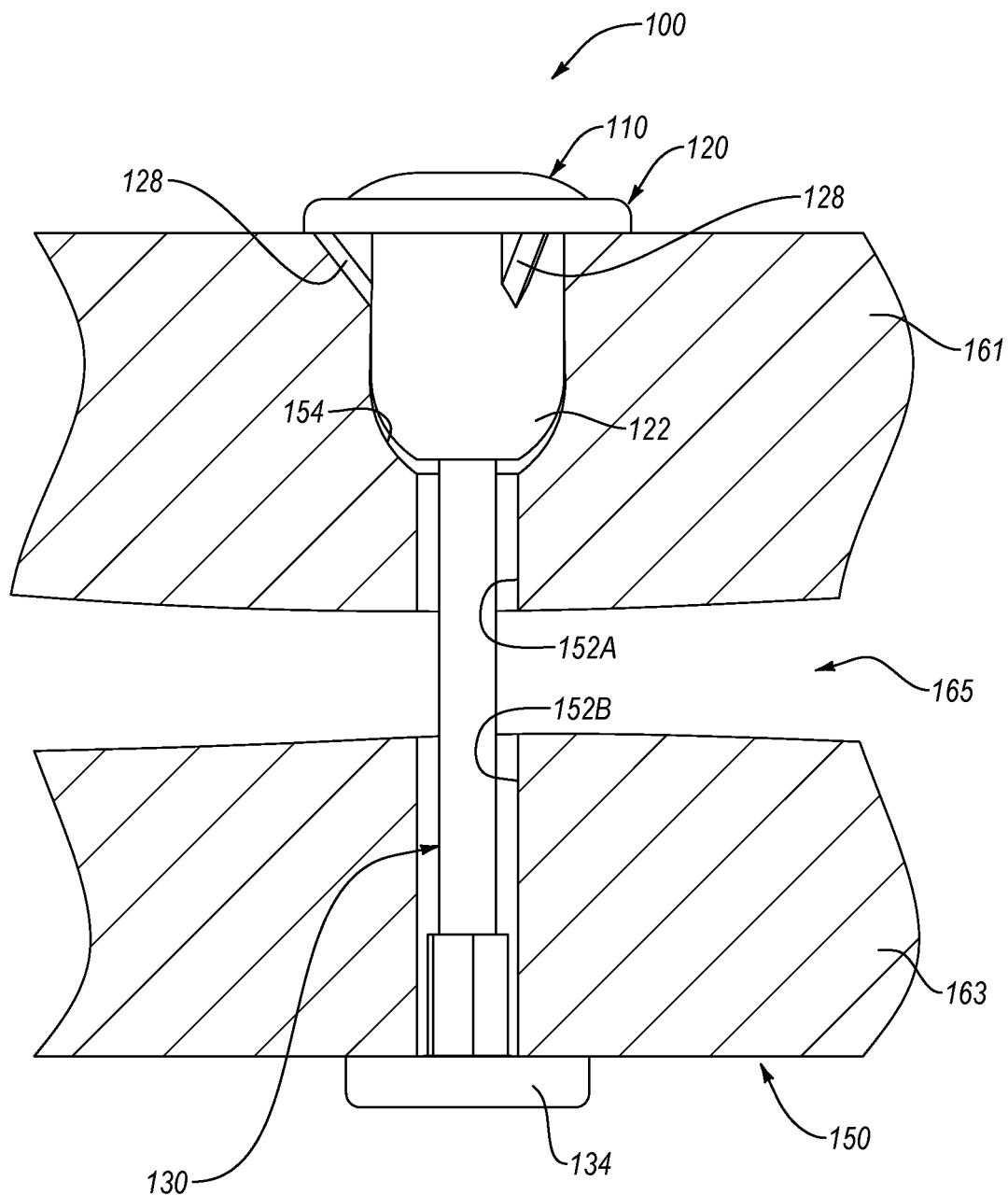
FIG. 14 is a partial cross-sectional side elevation view of the apparatus of FIG. 1, shown partially embedded in, and stabilizing relative to each other, two separate, spaced-apart bones, and with the set element of the apparatus in a fully inserted position in one of the bones, according to one or more examples of the present disclosure.
Figure 15:
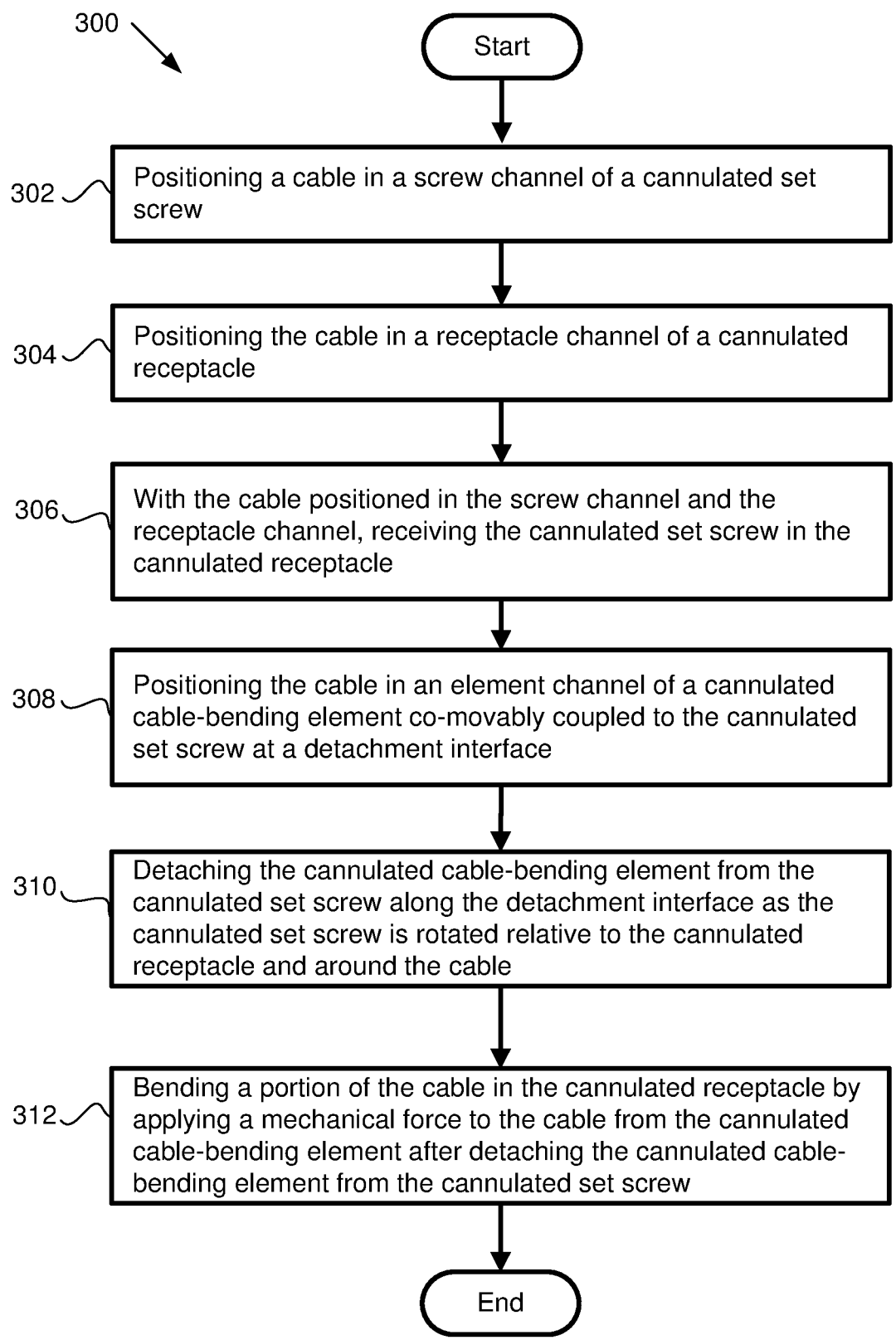
FIG. 15 is a schematic flow diagram of a method of crimping a cable, according to one or more examples of the present disclosure.
Figure 16:
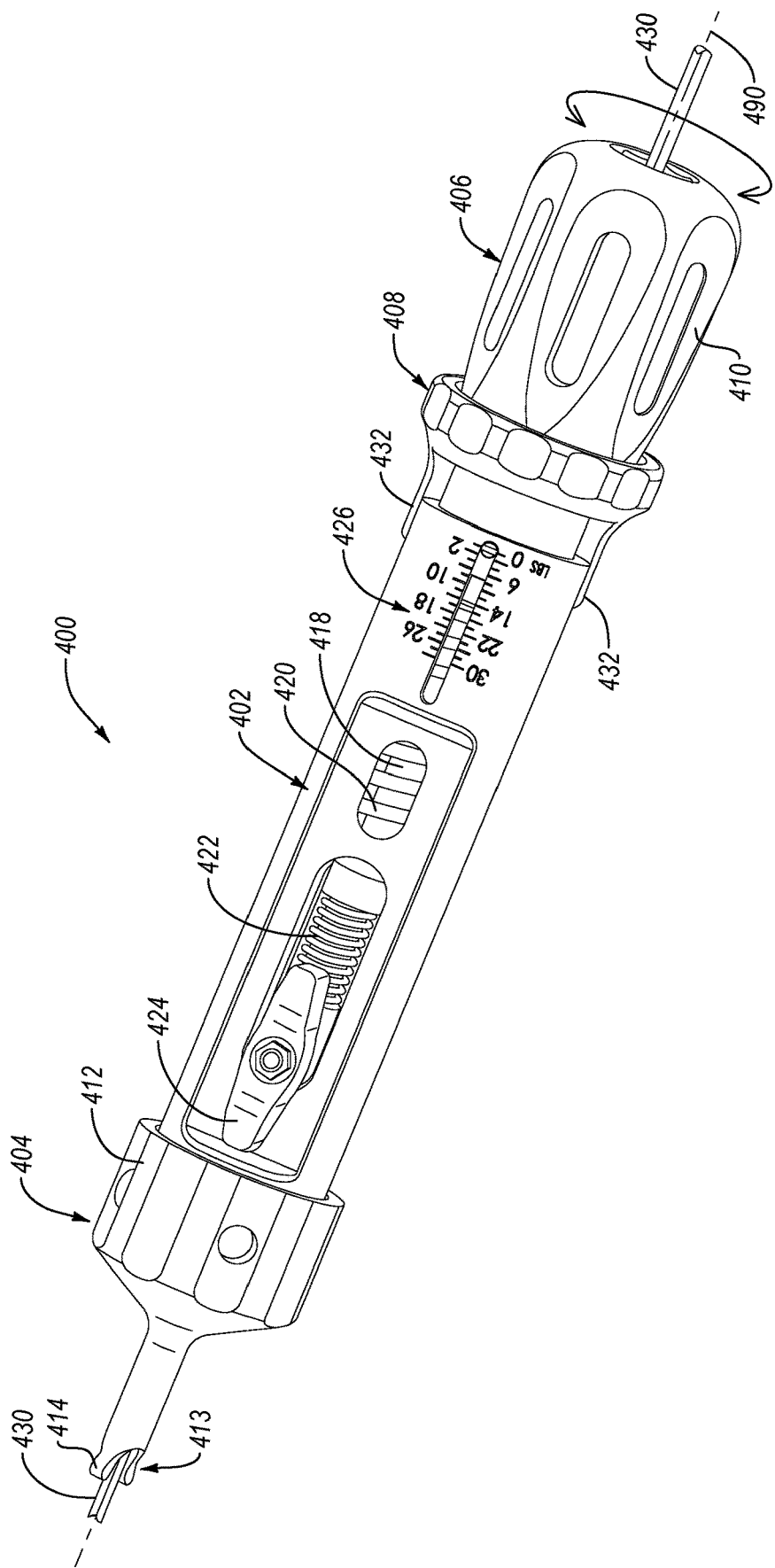
FIG. 16 is a perspective view of a cannulated tool, according to one or more examples of the present disclosure.

Referring to FIG. 14, the apparatus 100 is shown crimping the cable 130 in a bone 150, represented by a two bone configuration, as opposed to a single bone configuration as shown in FIGS. 1-6. The two bone configuration includes a first bone 161 and a second bone 163, which are spaced apart by a gap 165. The apparatus 100 helps to stabilize the first bone 161 and the second bone 163 relative to each other (and maintain the gap 165). The cannulated receptacle 120 is embedded within the first bone 161 and the stop 134 of the cable 130 is engaged with the second bone 163. The cable 130 passes through a first through-hole 152A (with two openings) formed in the first bone 161, the gap 165, and a second through-hole 152B (with two openings) formed in the second bone 163. Accordingly, the cable 130 spans the gap 165 between the first bone 161 and the second bone 163.

In one implementation, the first bone 161 is a tibia and the second bone 163 is a fibula of a patient. However, in other implementations, the first bone 161 and the second bone 163 can be any of various two bone configurations (e.g., radius and ulna) or two tissue configurations. Additionally, although two bones are shown, in other implementations, more than two bones can be stabilized relative to each other using the apparatus 100.

Referring to FIGS. 7-12, another embodiment of an apparatus 200 for crimping a cable, such as the cable 130, is shown. The apparatus 200 is analogous to the apparatus 100, with like numbers referring to like features. For example, analogous features of the apparatus 200 are labeled with 200-series numbers instead of 100-series numbers. Accordingly, the above description associated with the features of the apparatus 100 also applies to the like features of the apparatus 200 unless otherwise noted.

Like the apparatus 100, the apparatus 200 includes a cannulated cable-bending element 213 with a first portion 214 having a flat surface 244 oblique to a screw channel 240 of a cannulated set screw 212. However, unlike the apparatus 100, the cannulated cable-bending element 213 of the apparatus 200 also includes a second portion 260 coupled to the first portion 214. The second portion 260 protrudes from the first portion 214 such that the first portion 214 is between the second portion 260 and the cannulated set screw. Furthermore, the second portion 260 includes an elongate tube. An element channel 242 of the cannulated cable-bending element 213 extends entirely through the first portion 214 and the second portion 260. The elongate tube of the second portion 260 includes a second notch 264 formed into the elongate tube. In one implementation, the second notch 264 is located at an approximate midpoint of the elongate tube. Similar to the detachment interface 216, the second notch 264 is configured to create a weak point on the elongate tube for inducing a bend of the elongate tube at the second notch 264. According to some implementations, the second notch 264 occupies between about 5% and about 50% of a circumference of the elongate tube.

The elongate tube of the second portion 260 includes a first end, at the first portion 214, and a second end, opposite the first end. The second portion 260 further includes a first engagement element 262 at the second end of the elongate tube. The cannulated receptacle 220 further includes a second engagement element 225 formed into the interior surface 227 of the body 222. The second engagement element 225 is configured to engage the first engagement element 262 to constrain movement of the second end of the elongate tube in a direction perpendicular to the element channel 242 of the cannulated cable-bending element 213 when the cannulated set screw 212 is threadably received by the cannulated receptacle 220 (see, e.g., FIG. 12).

Like the apparatus 100, the apparatus 200 can form part of a system 201 used in a bone fixation procedure for fixating a bone. Operation of the system 201 is similar to that of the system 101. For example, as the set element 210 is rotated, a resistance to rotation of the first portion 214 of the cable-bending element 213 relative to the cannulated set screw 212 generates a shear force on the detachment interface 216. When the shear force exceeds the shear strength of the detachment interface 216, the first portion 214 shears away from the cannulated set screw 212 at the detachment interface 216. After the first portion 214 shears away from the cannulated set screw 212, because the first portion 214 is able to rotate relative to the cannulated set screw 212, further insertion of the cannulated set screw 212 into the cannulated receptacle 220 causes the inner end 280 of the cannulated set screw 212 to engage the flat surface 244 of the first portion 214. As indicated by a directional arrow in FIG. 12, engagement between the inner end 280 of the cannulated set screw 212 and the flat surface 244 of the first portion 214 causes the first portion 214 to rotate within the interior cavity 266 of the cannulated receptacle 220 about an axis perpendicular to the cable 130.

Figure 11:
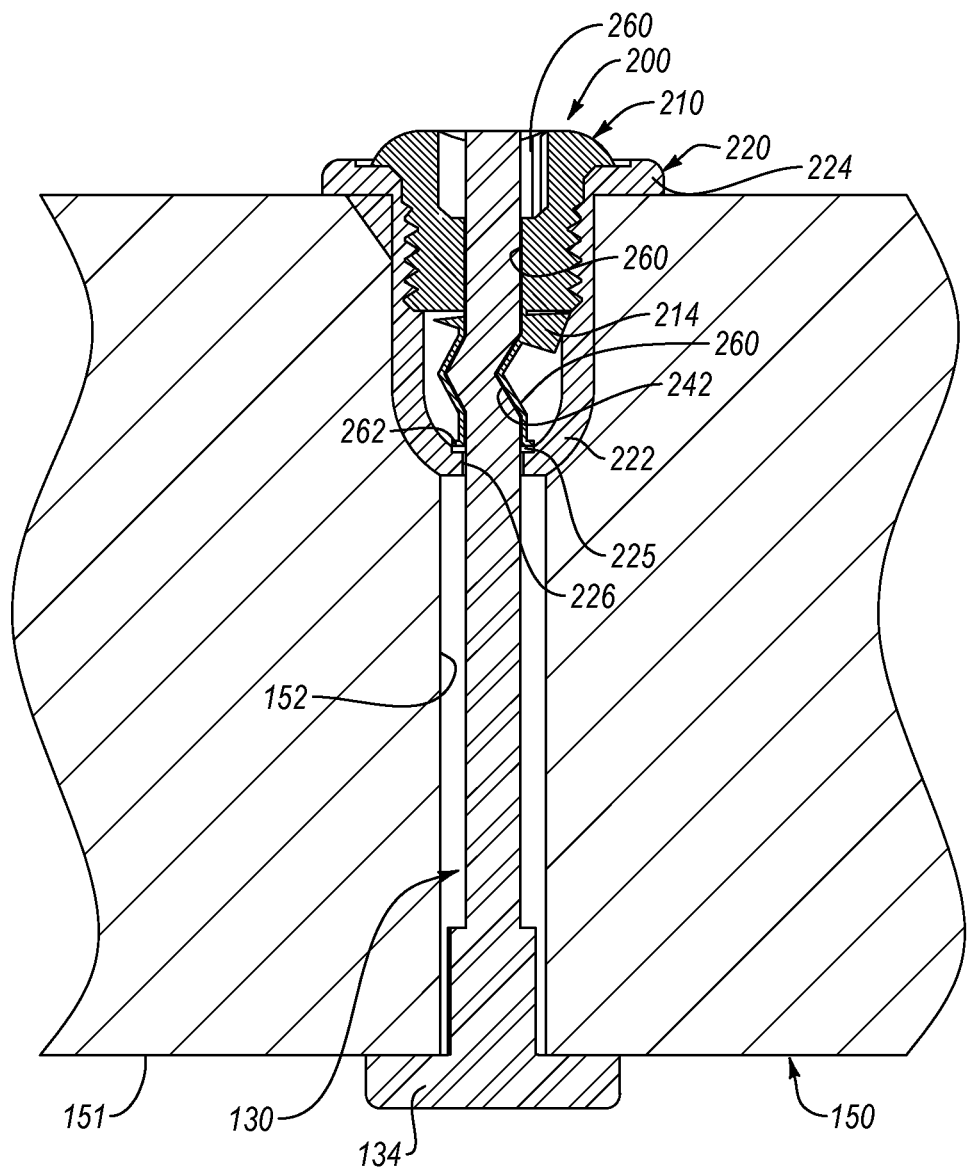
FIG. 11 is a cross-sectional side elevation view of the apparatus of FIG. 7, shown partially embedded in a bone and with the set element of the apparatus in a fully inserted position, according to one or more examples of the present disclosure.
Figure 12:
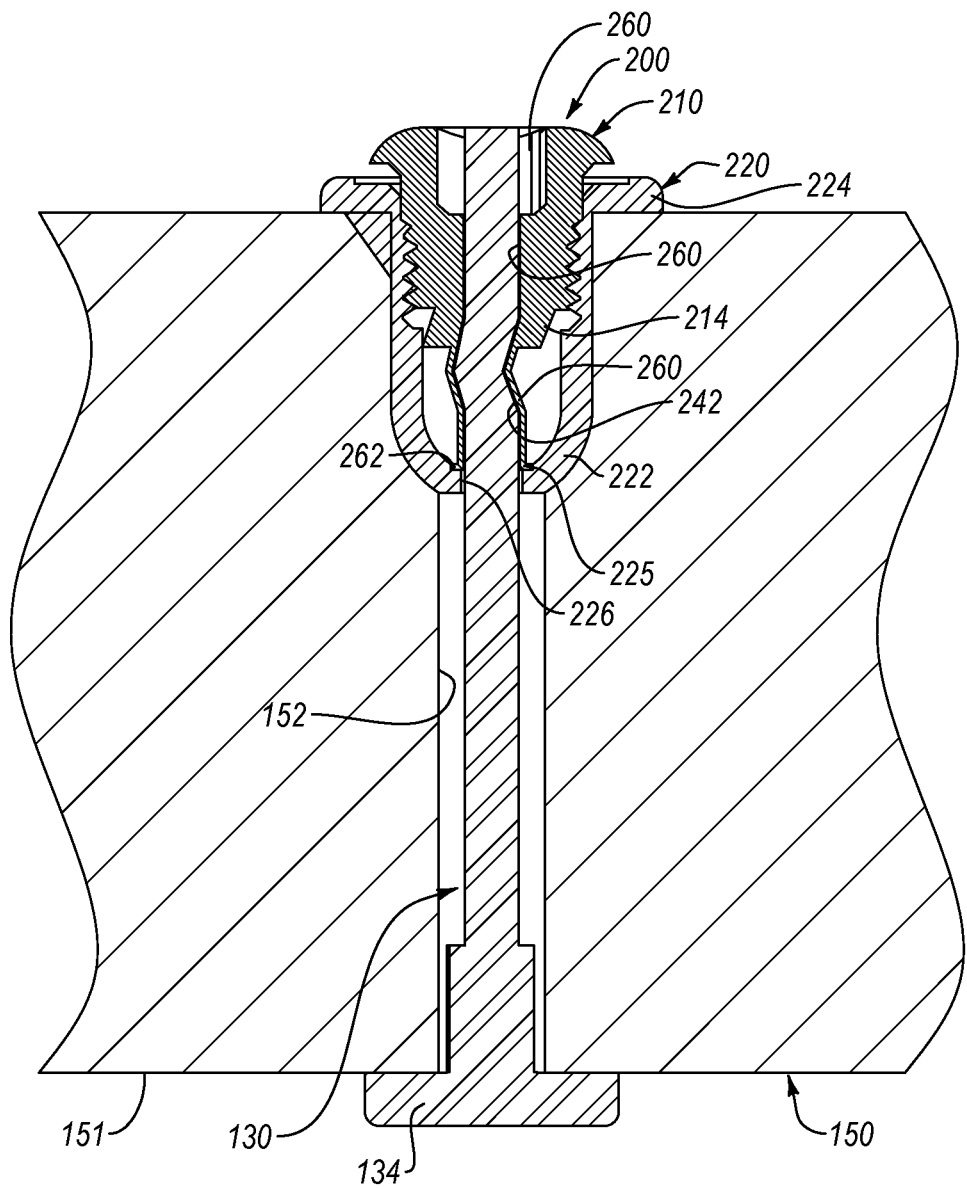
FIG. 12 is a cross-sectional side elevation view of the apparatus of FIG. 1, shown partially embedded in a bone and with the set element of the apparatus in a partially inserted position, according to one or more examples of the present disclosure.

Rotation of the first portion 214 in this manner not only correspondingly closes the first notch 215 and rotates the element channel 242 of the first portion 214, but also applies a rotational force to the elongate tube of the second portion 260. With the second end of the elongate tube constrained from movement, vis-à-vis the first engagement element 262 and the second engagement element 225, the rotational force causes the elongate tube to bend at the second notch 264 as shown in FIGS. 11 and 12. As the first portion 214 rotates about the axis perpendicular to the cable 230 and the second portion 260 bends at the second notch 264, the element channel 242 engages the portion of the cable 130 within the element channel 242 and forces this portion of the cable 230 to corresponding rotate and/or bend relative to adjacent portions of the cable 130.

At full insertion of the cannulated set screw 212 into the cannulated receptacle 220, the cable 130 is sufficiently bent that the bend 192 formed in the cable 130 prevent the cable 130 from sliding through the element channel 242. In this manner, the cable 130 is crimped within the cannulated receptacle 220 to prevent movement of the cable 130 relative to the apparatus 200 and the bone 150 and maintain any tension in the cable 130. The cable 130, after being crimped, can then be cut to remove excess portions of the cable 130 extending from the apparatus 200 as described above.

Referring to FIG. 14, according to one embodiment, a method 300 of crimping a cable is shown. The method 300 includes positioning a cable in a screw channel of a cannulated set screw at 302 and positioning the cable in a receptacle channel of a cannulated receptacle at 304. The method 300 also includes receiving the cannulated set screw in the cannulated receptacle, with the cable positioned in the screw channel and the receptacle channel, at 306. The method 300 additionally includes positioning the cable in an element channel of a cannulated cable-bending element co-movably coupled to the cannulated set screw at a detachment interface at 308. The method 300 further includes detaching the cannulated cable-bending element from the cannulated set screw along the detachment interface as the cannulated set screw is rotated relative to the cannulated receptacle and around the cable at 310. The method 300 also includes bending a portion of the cable in the cannulated receptacle by applying a mechanical force to the cable from the cannulated cable-bending element after detaching the cannulated cable-bending element from the cannulated set screw at 312.

As shown in FIGS. 16-26, another embodiment of a cannulated tool 400 is shown. Similar to the cannulated tool 170, the cannulated tool 400 includes a tool channel 460 extending an entire length of the cannulated tool 400. A cable 430, similar to the cable 130, is passable through the tool channel 460 of the cannulated tool 400 and concentric with the cannulated tool 400 while the cable 430 is crimped by the apparatus 100 or the apparatus 200. The cross-sectional size and shape of the tool channel 460 complements the cross-sectional size and shape of the cable 130. For example, the size of the tool channel 460 is at least as large as (e.g., slightly larger than) that of the cable 130. In this manner, the cable 130 is able to freely enter and pass through the tool channel 460 of the cannulated tool 400. The cannulated tool 400 is positionable relative to the apparatus 100 or the apparatus 200 such that the tool channel 460 of the cannulated tool 400 is concentric with the screw channel 140, 240 of the cannulated set screw 112, 212 and the element channel 142, 242 of the cannulated cable-bending element 113, 213.

Generally, the cannulated tool 400 is configured to both tension the cable 430 and rotatably drive the set element 110, 210 relative to the cannulated receptacle 120, 220. In this manner, the cannulated tool 400 provides at least two operations in a single tool. In some implementations, it may be difficult to maintain the cannulated receptacle 120, 220 stationary relative to the bone 150 as the set element 110, 210 is rotated related to the cannulated receptacle 120, 220. For example, in some implementations, such as for some bones, the fins 128, 228 of the cannulated receptacle 120, 220 may not be sufficient to prevent rotation of the cannulated receptacle 120, 220 relative to the bone if the torque transferred from the cannulated tool to the cannulated receptacle 120, 220 (via the set element 110, 210) exceeds the holding force of the fins 128, 228. Furthermore, when the cannulated receptacle 120, 220 rotates relative to the bone 150, then the set element 110, 210 cannot be rotated relative to the cannulated receptacle 120, 220 to rotatably drive the set element 110, 210 into the cannulated receptacle 120, 220.

Figure 18:
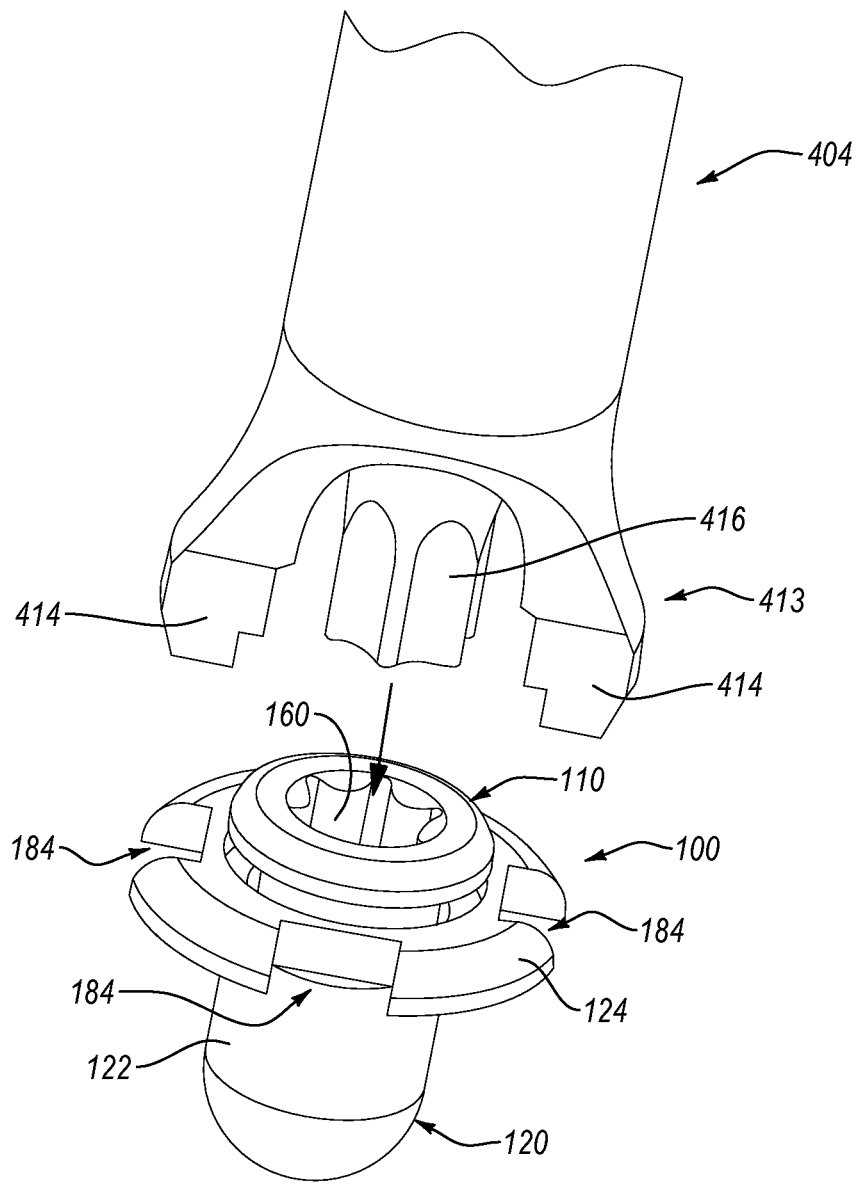
FIG. 18 is a perspective view of an anti-rotation feature disengaged from a cable crimping apparatus, according to one or more examples of the present disclosure.
Figure 19:
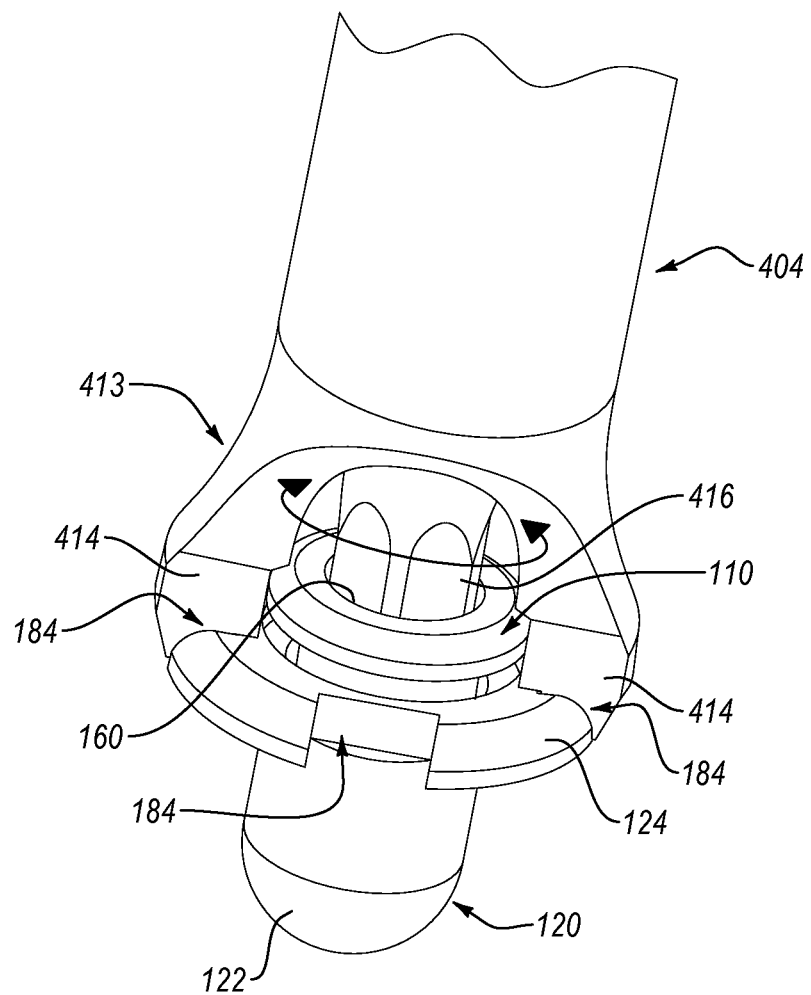
FIG. 19 is a perspective view of an anti-rotation feature engaged with a cable crimping apparatus, according to one or more examples of the present disclosure.
Figure 20:
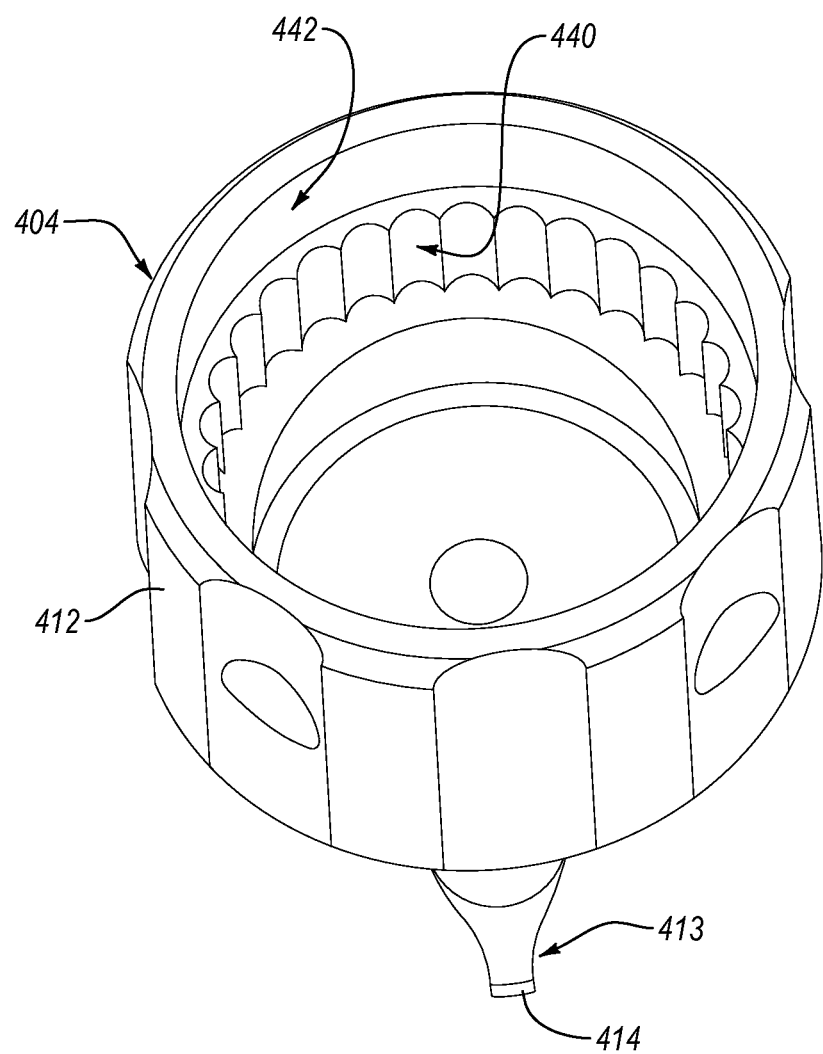
FIG. 20 is a perspective view of an anti-rotation knob of a cannulated tool, according to one or more examples of the present disclosure.

To ensure anti-rotation of the cannulated receptacle 120, 220 relative to the set element 110, 210, thus ensuring the set element 110, 210 is rotatably driven into the cannulated receptacle 120, 220 as the set element 110, 210 is rotated, the cannulated receptacle 120, 220 is modified to receive an anti-rotation feature 413 of the cannulated tool 400. Referring to FIG. 18, in one embodiment, the lip 124 of the cannulated receptacle 120 includes at least two notches 184 formed in an outer periphery of the lip 124. In the illustrated embodiment, the cannulated receptacle 120 includes four notches 184 or two pair of notches 184. The notches 184 of each pair of notches 184 are on opposite sides of the lip 124. The notches 184 are sized and shaped to matingly receive corresponding prongs 414 of the anti-rotation feature 413. As shown, the notches 184 are substantially square shaped. However, in other implementations, the notches 184 can have other shapes. In the illustrated embodiment, the anti-rotation feature 413 of the cannulated tool 400 includes two prongs 414 mateable with a pair of notches 184. However, in other embodiments, the anti-rotation feature 413 of the cannulated tool 400 may include four or more prongs 414 mateable with two or more pair of notches 184. In yet other implementations, the anti-rotation feature 413 of the cannulated tool 400 includes any of various engagement features configured to matingly engage any of various engagement features formed into the cannulated receptacle 120 to prevent rotation of the cannulated receptacle 120 relative to the anti-rotation feature 413 of the cannulated tool 400. Although referring to the cannulated receptacle 120 in particular, the cannulated receptacle 220 may also include notches in the lip 224 in a similar manner.

Figure 17:
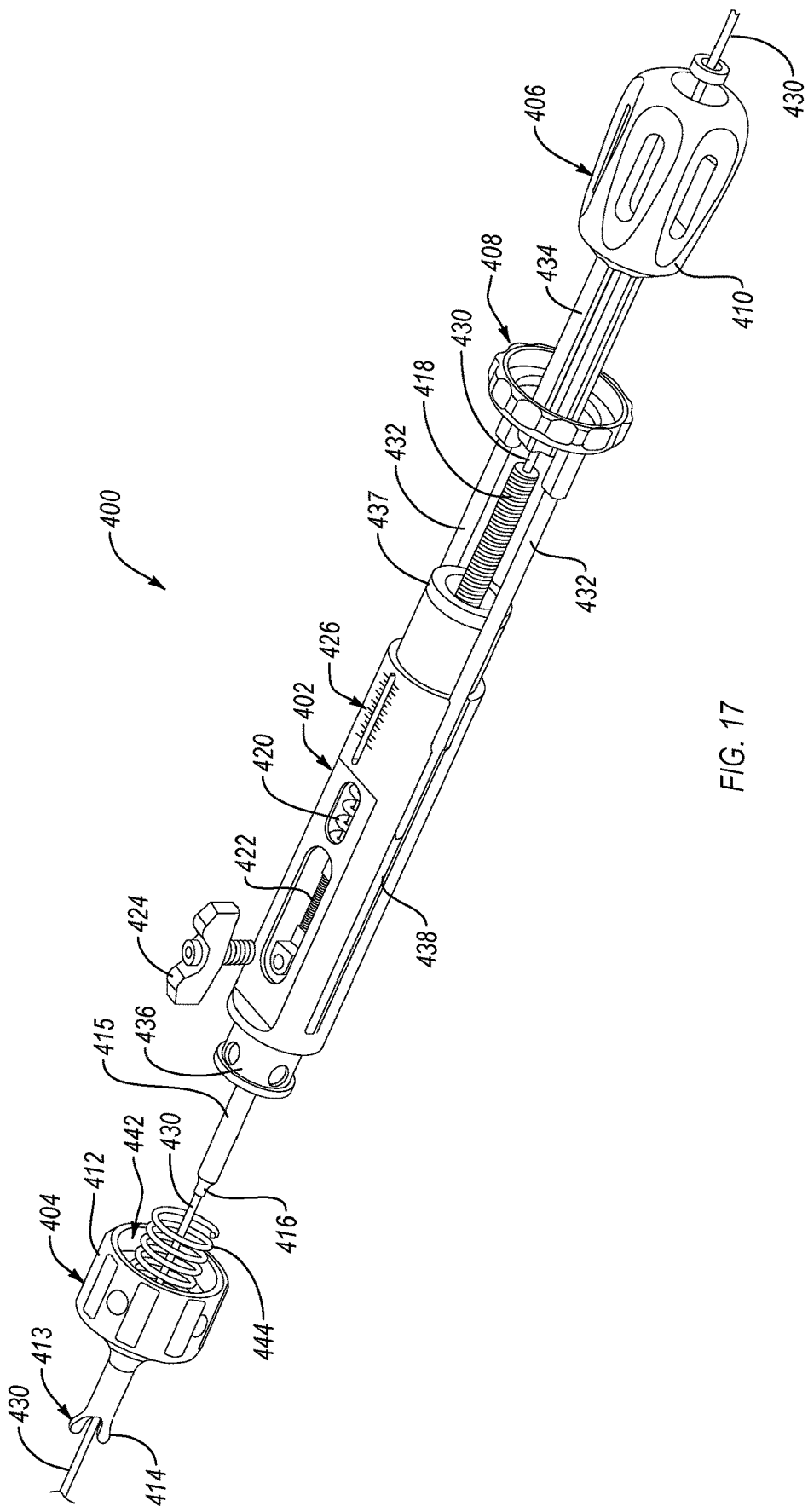
FIG. 17 is an exploded perspective view of a cannulated tool, according to one or more examples of the present disclosure.

The cannulated tool 400 includes a body 402. The body 402 is a substantially hollow body with a distal end portion 436 and a proximal end portion 437. Referring to FIG. 17, non-rotatably fixed to the distal end portion 436 of the body 402 is driving portion 415 that includes a screw engagement end 416. Accordingly, as the body 402 rotates, the screw engagement end 416 rotates. The screw engagement end 416 may have a male portion shaped and sized (e.g., star, hex, etc.) to be inserted into and matingly engage the tool recess 160, 260 of the cannulated set screw 112, 212 of the apparatus 100, 200, respectively. When engaged, rotation of the screw engagement end 178 rotates the tool recess 160, 260 and thus the cannulated set screw 112, 212. The tool channel 460 of the cannulated tool 400, which also extends through the driving portion 415, allows the body 402 and the driving portion 415 to rotate around the cable 430 without rotating the cable 430.

The cannulated tool 400 further includes an anti-rotation knob 404 that is rotatably attached to the distal end portion 436 of the body 402. In some implementations, the distal end portion 436 includes a lip that engages an internal groove formed in the anti-rotation knob 404. Engagement between the lip and the groove retains the anti-rotation knob 404 on the distal end portion 436 while allowing relative rotation of the anti-rotation knob 404 and the body 402. The anti-rotation knob 404 includes a grip 412 configured to enhance the gripability of the anti-rotation knob 404 by a user. The grip 412 may include apertures for receiving handles that help promote a secure hold on the anti-rotation knob 404. The anti-rotation knob 404 includes (e.g., is co-formed with) the anti-rotation feature 413. More specifically, the anti-rotation feature 413 is co-rotatable with the grip 412 such that rotation of the grip 412 also rotates the anti-rotation feature 413. The anti-rotation knob 404 defines a receptacle 442 for receiving the distal end portion 436 of the body 402. Formed into an interior periphery of the receptacle 442 are a plurality of slots 440. Each slot 440 is sized and arranged to receive an end of one of the latch pins 432 described below. The slots 440 are arranged in an annular fashion about the central axis 490 of the cannulated tool 400.

In some implementations, the cannulated tool 400 includes a spring 444, or other biasing element, between the anti-rotation knob 404 and the body 402 to allow for some restricted translational movement of the body 402 and the driving portion 415 relative to the anti-rotation knob 404. The relative translational movement allows the screw engagement end 416 of the driving portion 415 to be initially disengaged with the tool recess when the anti-rotation feature 413 is engaged with the cannulated receptacle 120 and then pushed into engagement with the tool recess. In other words, the relative translation movement facilitates engagement between the screw engagement end 416 and the tool recess and engagement between the anti-rotation feature 413 and the cannulated receptacle 120 to occur in two separate operations.

The cannulated tool 400 further includes a drive rod 418. The drive rod 418 is cannulated. In other words, the tool channel 460 of the cannulated tool 400 extends through the drive rod 418. The drive rod 418 is located within the body 402 (e.g., coaxial with the body 402) and extends from the distal end portion 436 to the proximal end portion 437. At the proximal end portion 437, the drive rod 418 includes an externally threaded portion. At the distal end portion 436, the drive rod 418 is configured to be selectively non-movably fixed to the cable 430 extending through the drive rod 418. The cannulated tool 400 includes a wing bolt 424 that is selectively rotatable to non-movably fix the cable 430 to the drive rod 418. In one implementation, the wing bolt 424 is tightened to clamp the cable 430 against the drive rod 418. The drive rod 418 is translationally movable along the body 402 but is non-rotatable relative to the body 402.

The cannulated tool 400 additional includes a tension measurement system that is configured to measure the tension in the cable 430. The tension measurement system includes one or more springs, such as first spring 422 and second spring 420. The springs 420, 422 wrap around the drive rod 418 and are coupled to the drive rod 418 and the body 402 such that movement of the drive rod 418 along the body 402 compresses the springs 420, 422. With the cable 430 fixed to the drive rod 418 by the wing bolt 424, movement of the drive rod 418 along the body 402 tensions the cable 430. Based on the characteristics of the springs 420, 422 (e.g., spring constant, etc.), the distance the drive rod 418 travels, which corresponds with the distance the springs 420, 422 are compressed, can be used to determine the tension force or load placed on the cable 430. The cannulated tool 400 additionally includes a tension indicator 426 that provides a visual indication of the tension force placed on the cable 430. The tension indicator 426 includes tension force markings on the body 402 and a portion of the second spring 420 that is movable along the tension force markings as the second spring 420 is compressed.

The cannulated tool 400 also includes an actuator 406 that includes a knob 410 and a neck 434 co-rotatably coupled to the knob 410. The knob 410 may include grip-enhancing features to promote manual rotation of the knob 410. The neck 434 includes an internally threaded channel with threads configured to threadably engage the threads of the externally threaded portion of the drive rod 418. The actuator 406 further includes teeth 450 formed in a distal end of the knob 410.

The cannulated tool 400 is selectively switchable between a screw driving mode and a cable tensioning mode by shifting a clutch ring 408, translationally along the central axis 490 of the cannulated tool 400, between a driving position and a tensioning position. The clutch ring 408 encircles the body 102 and may include grip-enhancing features about a periphery of the clutch ring 408. The clutch ring 408 includes two latch pins 432 fixed to the clutch ring 408 on opposite sides of the clutch ring 408. The latch pins 432 are elongated in a direction parallel to the central axis 490 of the cannulated tool 400. The latch pins 432 are slidably engaged with slots 438 formed in an outer surface of the body 402. As the clutch ring 408 moves linearly along the central axis 490, the latch pins 432 move linearly along the slots 438. Moreover, engagement between the latch pins 432 and the slots 438 in the body 402 ensure co-rotation of the clutch ring 408 and the body 402. The clutch ring 408 further includes teeth 452 formed in the proximal end of the clutch ring 408. The teeth 452 are configured to engage the teeth 450 formed in the distal end of the knob 410 to prevent relative rotation between the clutch ring 408 and the knob 410.

Figure 22:
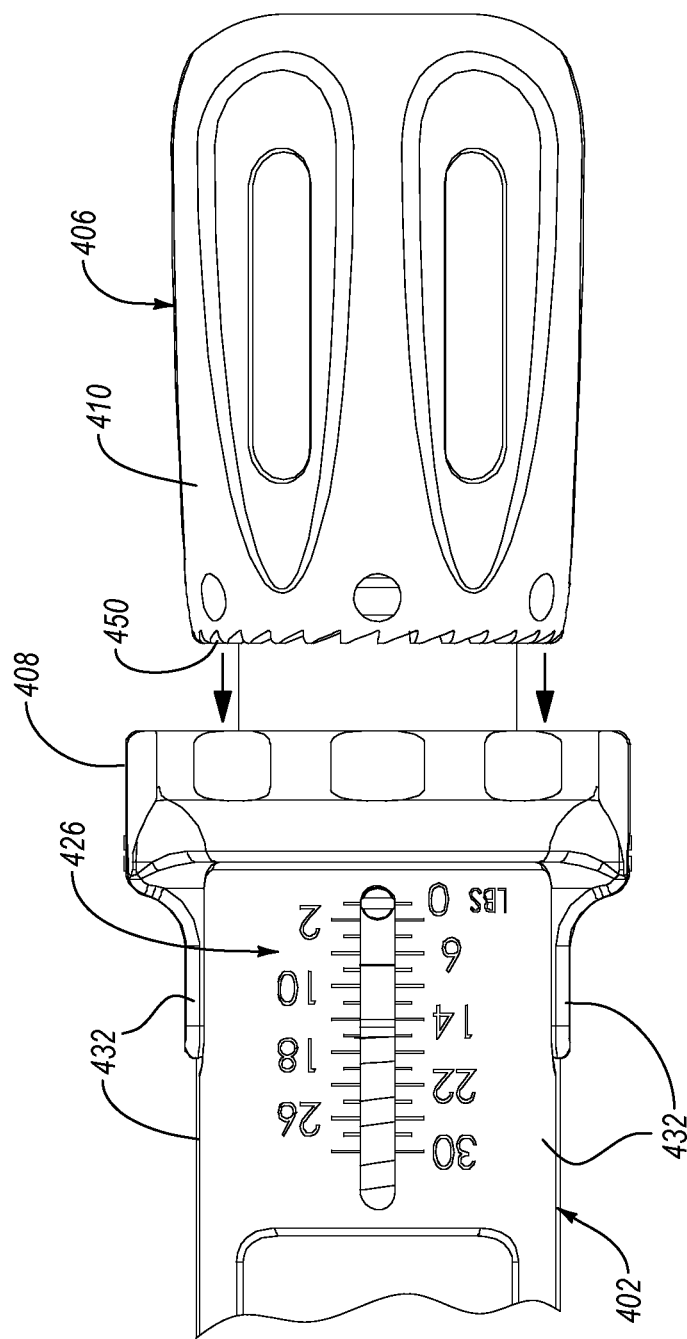
FIG. 22 is a side view of a clutch ring of a cannulated tool in a tensioning position, according to one or more examples of the present disclosure.
Figure 23:
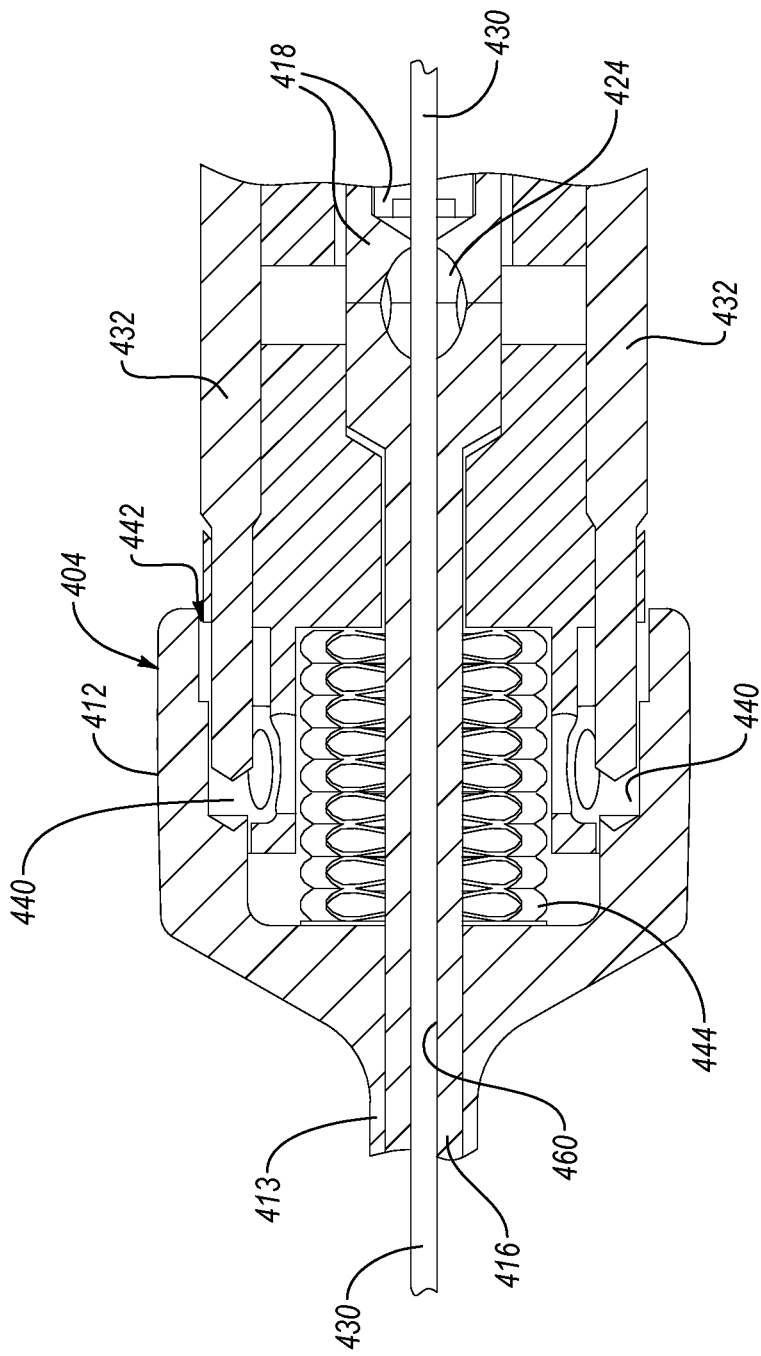
FIG. 23 is a cross-sectional side view of a distal end of a cannulated tool, according to one or more examples of the present disclosure.
Figure 24:
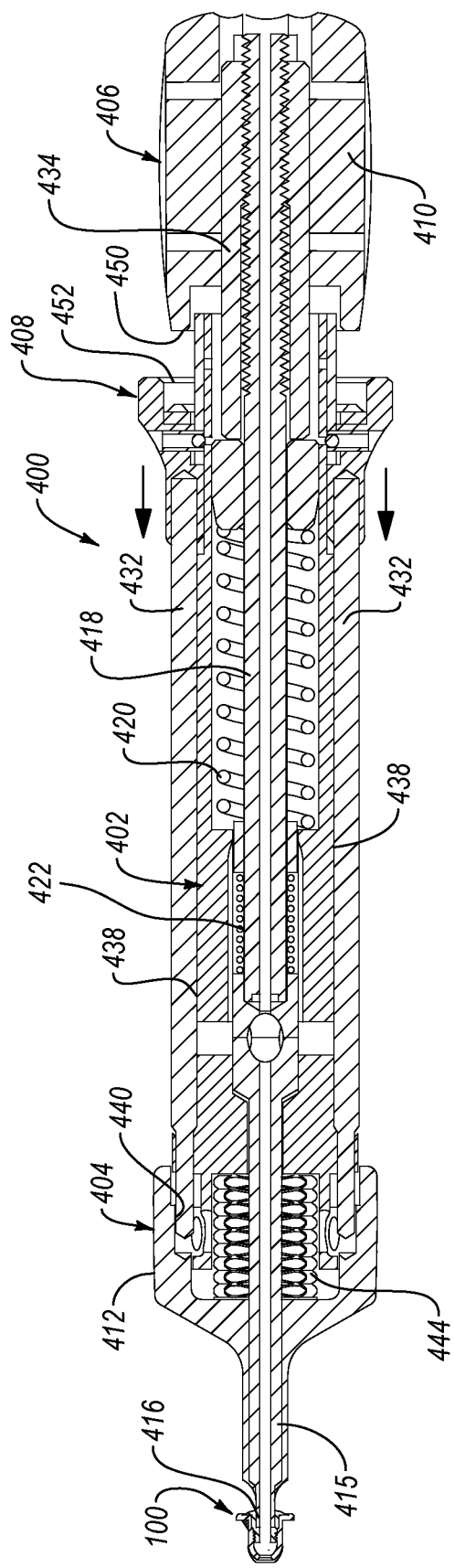
FIG. 24 is a cross-sectional side view of a cannulated tool, in a tensioning mode, according to one or more examples of the present disclosure.

Referring to FIGS. 22 and 24, in the tensioning position, the clutch ring 408 is shifted towards the distal end 436 of the body 402 away from the knob 410 as indicated by directional arrows. In some implementations, the body 402 include indicia of the tensioning mode, which is visible only when the clutch ring 408 is in the tensioning position. The body 402 also includes indicia of the driving mode, which is covered up by the clutch ring 408 when the clutch ring 408 is in the tensioning position. Because the clutch ring 408 is spaced apart from the knob 410 in the tensioning position, the knob 410 is free to rotate relative to the clutch ring 408 and thus relative to the body 402 and the driving portion 415. Relative rotation between the knob 410 and the body 402 is promoted by engagement between the latch pins 432 and the slots 440 of the anti-rotation knob 404, which is manually held stationary by a user to prevent rotation of the anti-rotation knob 404 relative to the bone 150. As the knob 410 is rotated, with the clutch ring 408 in the tensioning position, threaded engagement between the external threads of the drive rod 418 and the internal threads of the neck 434, the drive rod 418 moves linearly away from the distal end 432 of the body 402. Furthermore, with the wing bolt 424 non-movably fixing the cable 430 to the drive rod 418, the cable 430 is pulled away from the distal end 432 of the body 402 to place the cable 430 in tension. The knob 410 is rotated until the cable 430 is under a desirable tension, such as indicated by the tension indicator 426.

Figure 21:
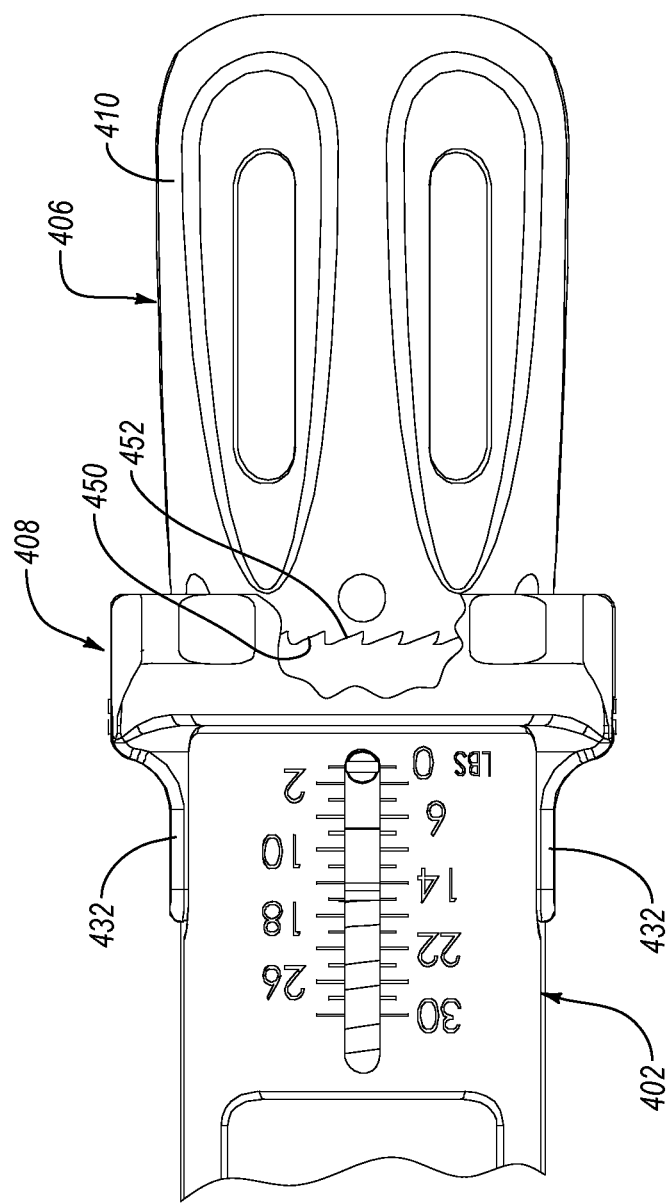
FIG. 21 is a partially transparent side view of a clutch ring of a cannulated tool in a driving position, according to one or more examples of the present disclosure.
Figure 25:
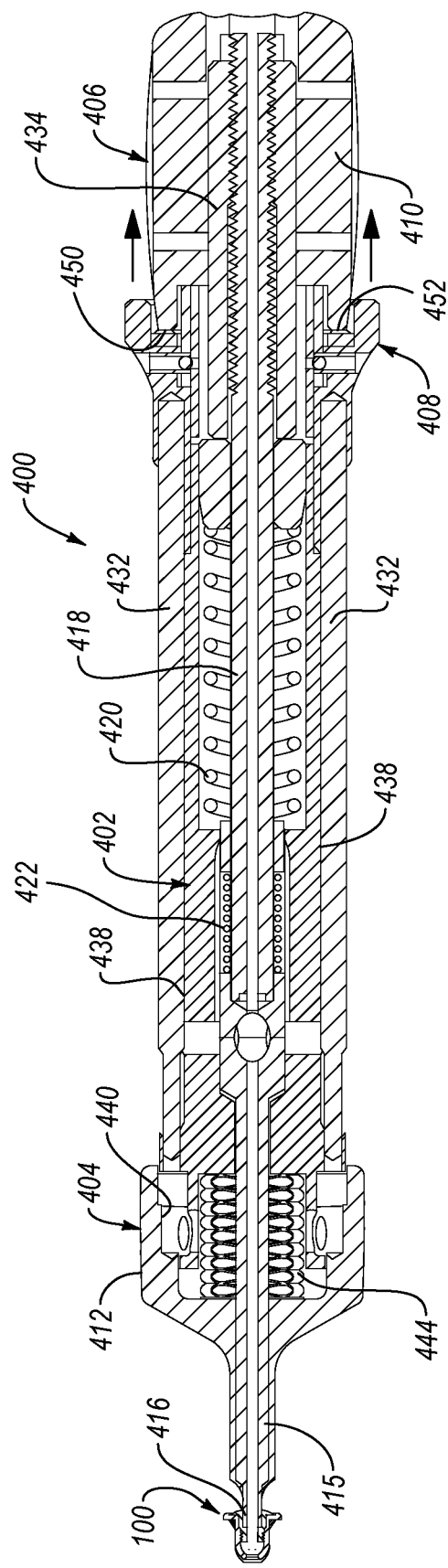
FIG. 25 is a cross-sectional side view of a cannulated tool, in a driving mode, according to one or more examples of the present disclosure.
Figure 26:
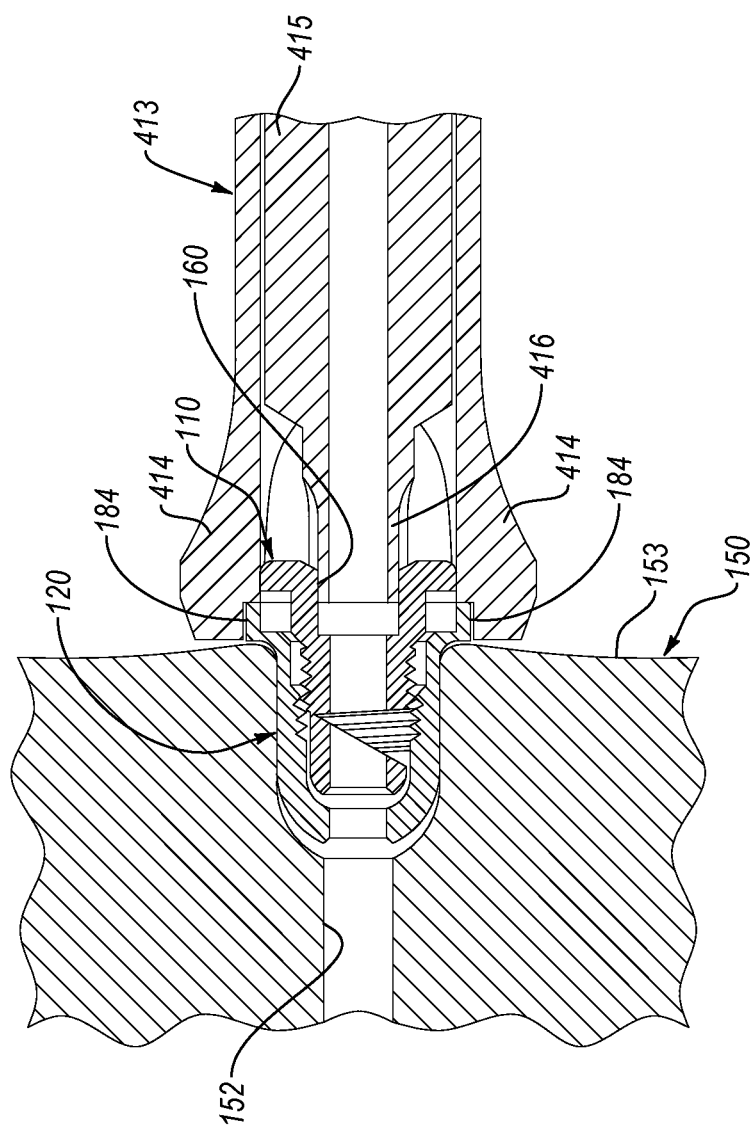
FIG. 26 is a cross-sectional side view of a distal end of a cannulated tool engaged with a cable crimping apparatus in a bone, according to one or more examples of the present disclosure.

Referring to FIGS. 21 and 25, once the cable 430 is tensioned to a desirable tension, the clutch ring 408 is shifted away from distal end 436 of the body 402 toward the knob 410 as indicated by directional arrows. The clutch ring 408 is placed in the driving position when the teeth 152 of the clutch ring 408 engage the teeth 450 of the knob 410. Also, moving the clutch ring 408 into the driving position also disengages the latch pins 432 from the slots 440 in the anti-rotation knob 404. In the driving position, the tensioning mode indicia is covered up by the clutch ring 408 and the driving mode indicia is visible. With the clutch ring 408 in the driving position, rotation of the knob 406 rotates the body 402. Moreover, with the anti-rotation knob 404 manually held stationary by a user, rotation of the knob 406 rotates the body 402, and thus the screw engagement end 416 of the driving portion 415, relative to the anti-rotation knob 404 relative to the bone 150. Before rotating the knob 406 in the driving mode, the screw engagement end 416 is brought into engagement with the tool recess 160 of the cannulated set screw 112 such that rotation of the knob 406 also rotates the cannulated set screw 112. With the anti-rotation knob 404 held stationary relative to the bone 150 (see FIG. 26), engagement between the prongs 414 of the anti-rotation feature 413 and the notches 184 of the cannulated receptacle 120 acts to hold stationary the cannulated receptacle 120 relative to the bone 150 as the cannulated set screw 112 is rotated relative to the bone 150 to drive the cannulated set screw 112 into the cannulated receptacle 120 to crimp the cable 430 while in tension. After the cable 430 is crimped, the tension can be removed by loosening the wing nut 424 and sliding the cannulated tool 400 off of the cable 430. The cable 430 can then be cut at the set screw 112. In other implementations, the cable 430 can be cut while tensioned by the cannulated tool 400, such as via a cutting mechanism built into the cannulated tool 400.

Figure 27:
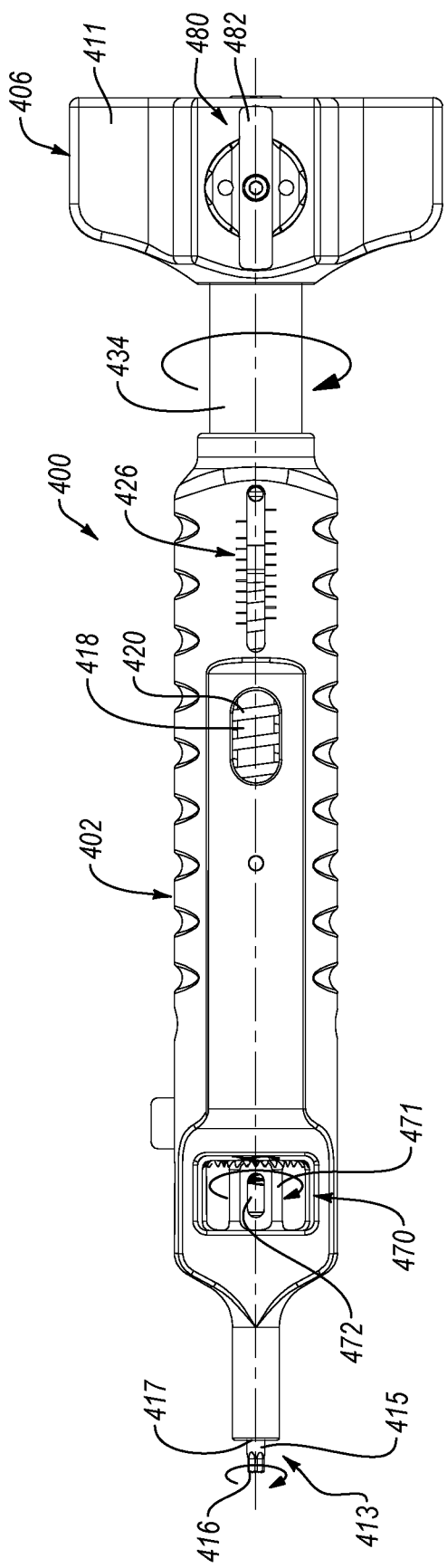
FIG. 27 is a top plan view of a cannulated tool, according to one or more examples of the present disclosure.
Figure 28:
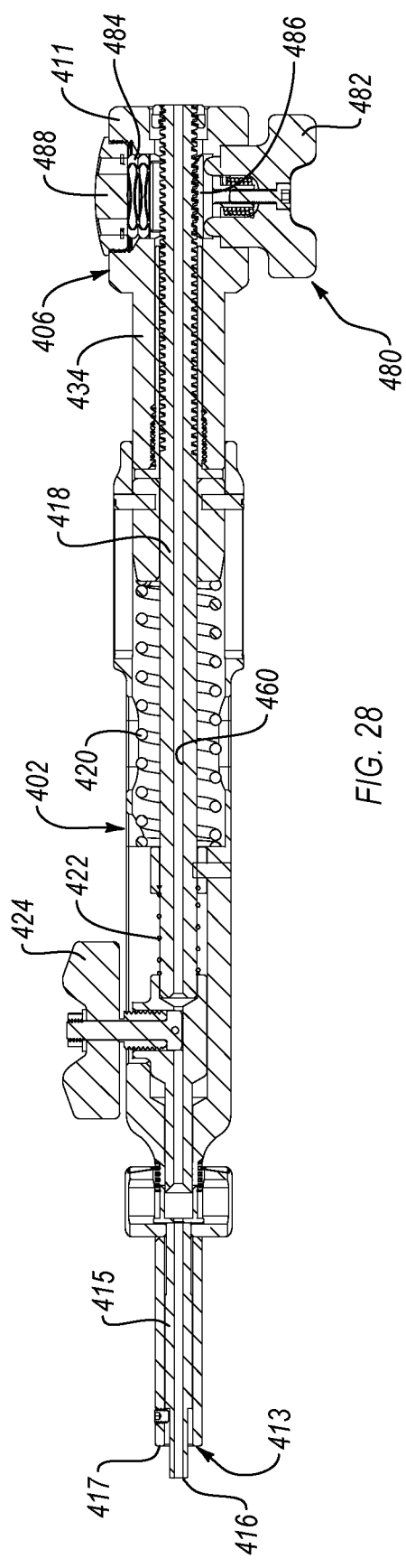
FIG. 28 is a cross-sectional side view of a cannulated tool, according to one or more examples of the present disclosure.

Referring to FIGS. 27 and 28, another example of the cannulated tool 400 is shown. The cannulated tool 400 of FIGS. 27 and 28 is similar to the cannulated tool 400 of FIGS. 16-26, with like numbers referring to like features. Unless otherwise indicated, the features and operation of the cannulated tool 400 of FIGS. 27 and 28 is the same as or similar to the feature and operation of the cannulated tool 400 of FIGS. 16-26. For example, the cannulated tool 400 of FIGS. 27 and 28 includes a body 402, an actuator 406 with a handle 411 and a neck 434, an anti-rotation feature 413 with a receptacle 417 that is engageable with cannulated receptacle 120, a driving portion 415 with a screw engagement end 416, a drive rod 418, a wing bolt 424, a tension measurement system with a first spring 422, a second spring 420, and a tension indicator 426, and a tool channel 460. Accordingly, unless otherwise indicated, the above-presented description of the features and operation of the cannulated tool 400 of FIGS. 16-26 is equally applicable to the cannulated tool 400 of FIGS. 27 and 28.

Unlike the cannulated tool 400 of FIGS. 16-26, the cannulated tool 400 of FIGS. 27 and 28 is not selectively switchable between a screw driving mode and a cable tensioning mode by shifting a clutch ring 408. Rather, the cannulated tool 400 of FIGS. 27 and 28 includes screw driving features and cable tensioning features that are operable independently of each other and can be operable concurrently of each other. In other words, the cable tensioning features, such as the actuator 406, are decoupled from the screw driving features, such as a screw driving mechanism 470. More specifically, rotation of the handle 411 of the actuator 406, as shown, tensions a cable 430 fixed to the drive rod 418 by the wing bolt 424, but does not, in any configuration, rotate the driving portion 415 relative to the body 402. Instead, only the screw driving mechanism 470, located closer to the driving portion 415 than the handle 411, rotates the driving portion 415 relative to the body 402 as shown.

The cable tensioning features of the cannulated tool 400 of FIGS. 27 and 28 further includes a tension quick-release mechanism 480 that is configured to quickly release tension in a tensioned cable 430. The tension quick-release mechanism 480 includes a handle 482, a clutch pad 486, and a spring 484. Moreover, the tension quick-release mechanism 480 is integrated into the actuator 406, such as the handle 411 of the actuator 406. The handle 482 is rotatable between an engaged position and a disengagement position. In some examples, the handle 482 is rotatable between the engaged position and the disengagement position by rotating the handle 482 between a quarter turn and a half turn. In the engaged position, the handle 482 forces the clutch pad 486 into threaded engagement with the drive rod 418. Threaded engagement between the clutch pad 486 and the drive rod 418 prevents the drive rod 418 from translationally moving in a detensioning direction toward the screw engagement end 416. The spring 484, which is retained in place by a cap 488, biases the clutch pad 486 into engagement with the drive rod 418.

When the handle 482 is in the engaged position, the drive rod 418 is able to move translationally in a tensioning direction away from the screw engagement end 416. However, rotating the handle 482 into the disengagement position threadably disengages the clutch pad 486 from the drive rod 418, which allows the drive rod 418 to translationally move in the detensioning direction toward the screw engagement end 416 thereby releasing the tension in the cable 430 fixed to the drive rod 418. With tension built-up in the cable 430, once the clutch pad 486 is disengaged from the drive rod 418, the force of the tension causes a rapid translational movement of the drive rod 418 in the detensioning direction and thus a rapid release of tension in the cable 430. Accordingly, instead of rotating the handle 411 of the actuator 406 in a reverse direction to proportionally and slowly release tension in cable 430, the tension quick-release mechanism 480 allows a rapid release of tension in the cable 430 in response to a non-proportional and relatively minimal rotation of the handle 482.

The screw driving mechanism 470 is directly and rotatably coupled to the driving portion 415. In the illustrated example of FIG. 27, the screw driving mechanism 470 includes a drive wheel 470 co-rotatably coupled to the driving portion 415. The drive wheel 470 includes a tool engagement feature 472 (e.g., a slot, recess, or receptacle), which is configured to receive a driving tool (not shown). With the driving tool received in or engaged with the tool engagement feature 472, the driving tool can be pivoted about an axis (e.g., the central axis 490) concentric with the channel 460 to rotate the driving portion 415 and the screw engagement end 416 about the same axis. Generally, the driving tool is oriented perpendicularly relative to the channel 460. In some examples, the drive wheel 470 includes multiple tool engagement features 472 and the driving tool is inserted into one tool engagement feature 472, used to rotate a partial turn of the drive wheel 470, removed and inserted into another tool engagement feature 472 to further rotate a partial turn of the drive wheel 470. This process can be repeated until the driving portion 415 and corresponding cannulated set screw have been adequately turned.

Figure 29:
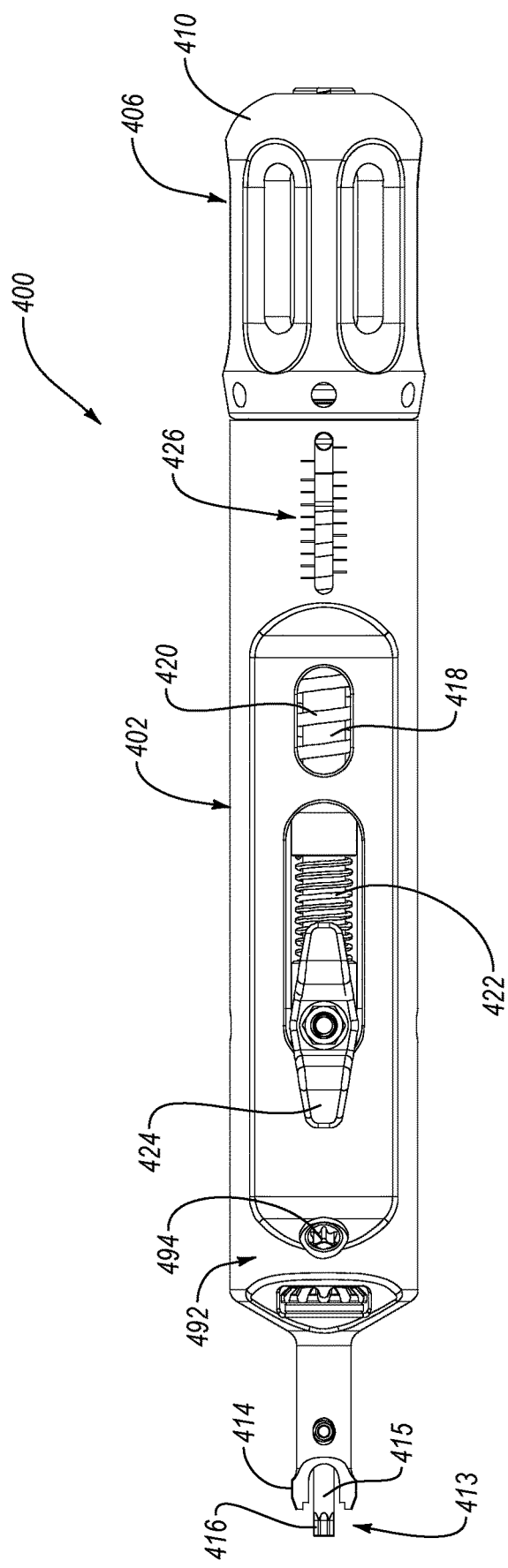
FIG. 29 is a top plan view of a cannulated tool, according to one or more examples of the present disclosure.
Figure 30:
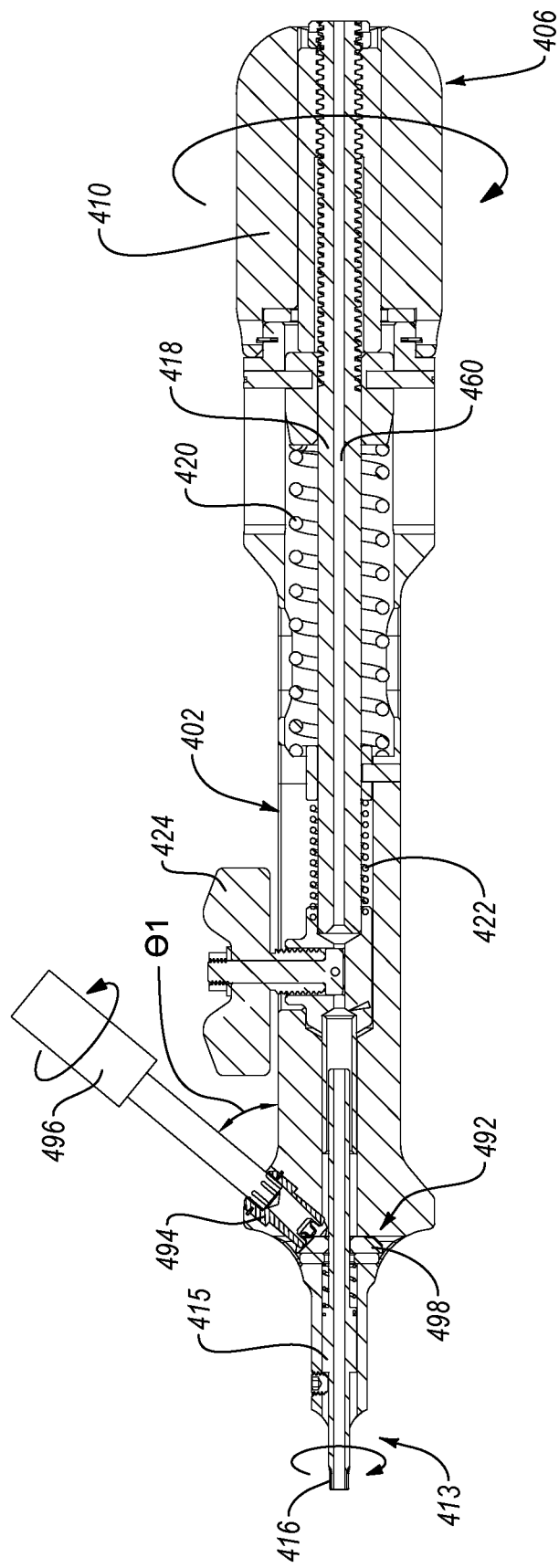
FIG. 30 is a cross-sectional side view of a cannulated tool, according to one or more examples of the present disclosure.

Referring to FIGS. 29 and 30, another example of the cannulated tool 400 is shown. The cannulated tool 400 of FIGS. 29 and 30 is similar to the cannulated tool 400 of FIGS. 16-26 and the cannulated tool 400 of FIGS. 27 and 28, with like numbers referring to like features. Unless otherwise indicated, the features and operation of the cannulated tool 400 of FIGS. 29 and 30 is the same as or similar to the feature and operation of the cannulated tool 400 of FIGS. 16-28. For example, the cannulated tool 400 of FIGS. 29 and 30 includes a body 402, an actuator 406 with a knob 410, an anti-rotation feature 413 with prongs 414 that are engageable with cannulated receptacle 120, a driving portion 415 with a screw engagement end 416, a drive rod 418, a wing bolt 424, a tension measurement system with a first spring 422, a second spring 420, and a tension indicator 426, and a tool channel 460. Accordingly, unless otherwise indicated, the above-presented description of the features and operation of the cannulated tool 400 of FIGS. 16-28 is equally applicable to the cannulated tool 400 of FIGS. 29 and 30.

Although the actuator 406 of the cannulated tool 400 illustrated in FIGS. 29 and 30 does not include a tension quick-release mechanism 480, in some examples, a tension quick-release mechanism 480 can be incorporated into the actuator 406 of the cannulated tool 400 of FIGS. 29 and 30. Moreover, like the cannulated tool 400 of FIGS. 27 and 28, the cannulated tool 400 of FIGS. 29 and 30 is not selectively switchable between a screw driving mode and a cable tensioning mode by shifting a clutch ring 408, but rather includes screw driving features and cable tensioning features that are operable independently and concurrently of each other.

The cannulated tool 400 of FIGS. 29 and 30 includes a screw driving mechanism 492. Like the screw driving mechanism 470 of the cannulated tool 400 of FIGS. 27 and 28, the screw driving mechanism 492 is directly and rotatably coupled to the driving portion 415. However, unlike the screw driving mechanism 470, the screw driving mechanism 492 facilitates engagement with a driving tool 496 that is oriented at an oblique angle θ1 relative to the channel 460. Being able to orient the driving tool 496 at the oblique angle θ1 when driving the screw driving mechanism 492 promotes additional room, away from the tissue of a patient, for a practitioner to grasp and operate the driving tool 496.

The screw driving mechanism 492 includes a first bevel gear 494 (e.g., drive gear) and a second bevel gear 498 (e.g., driven gear). The first bevel gear 494 is in gear meshing engagement with the second bevel gear 498 to form a gear chain. The second bevel gear 498 is co-rotatably coupled to the driving portion 415 and thus rotates about an axis (e.g., the central axis 490) concentric with the channel 460. In contrast, the first bevel gear 494 rotates about an axis that is oblique to the central axis 490 or the channel 460 by the oblique angle θ1. The oblique angle θ1 is less than 90-degrees. In some examples, the oblique angle θ1 is no more than 45-degrees. The first bevel gear 494 includes a tool engagement recess for receiving an engagement end of the driving tool 496. When engaged with the first bevel gear 494, rotation of the driving tool 496 about its rotational axis correspondingly rotates the first bevel gear 494 about its rotational axis.

Rotation of the second bevel gear 498, and thus the driving portion 415, is caused by rotation of the second bevel gear 498 by the driving tool 496. Because of the additional room created by angling the second bevel gear 498, the driving tool 496 can also be angled, which facilitates the use of driving tools that are rotatable about a rotational axis, such as a screwdriver, as opposed to a driving tool that is pivoted about an axis, such as a wrench. Accordingly, in some examples, the driving tool 496 is a screwdriver that is rotatable about its central axis, being concentric with the rotational axis of the first bevel gear 494 when engaged with the first bevel gear 494. Based on the foregoing, the screw driving mechanism 492 enables the cannulated tool 400 to be approached by a driving tool 496 at an oblique angle, rather than a right angle, which promotes ease in engaging and driving the screw driving mechanism 492.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A cannulated tool through which a cable is passable, the cannulated tool comprising:
    a body;
    a screw driving feature, rotatable relative to the body;
    an anti-rotation feature, rotatable relative to the screw driving feature;
    a cable tensioning feature, configured to tension the cable when passed through the cannulated tool; and
    a central axis;
    wherein:
        the screw driving feature comprises a drive gear and a driven gear;
        the driven gear is rotatable about a first axis that is concentric with the central axis of the cannulated tool; and
        the drive gear is rotatable about a second axis that is oblique to the central axis of the cannulated tool.

2. The cannulated tool according to claim 1, wherein the cable tensioning feature comprises an actuator that is rotatable to tension the cable.

3. The cannulated tool according to claim 2, further comprising a tension quick-release mechanism that is selectively operable to release all tension in the cable independently of the cable tensioning feature.

4. The cannulated tool according to claim 3, wherein the quick-release mechanism comprises a handle that is rotatable to release all tension in the cable.

5. The cannulated tool according to claim 4, wherein the handle is rotatable, at most, a half turn to release all tension in the cable.

6. The cannulated tool according to claim 3, wherein the tension quick-release mechanism is integrated into the actuator.

7. The cannulated tool according to claim 6, wherein:
    the actuator comprises a handle; and
    the tension quick-release mechanism is integrated into the handle of the actuator.

8. The cannulated tool according to claim 1, wherein the second axis is angled at an angle no more than 45-degrees relative to the central axis of the cannulated tool.

9. The cannulated tool according to claim 1, further comprising a tension indicator configured to provide a visual indication of a tension force placed on the cable when passed through the cannulated tool and tensioned by the cable tensioning feature.

10. A system for crimping a cable, the system comprising:
    a cannulated set screw, comprising a screw channel;
    a cannulated receptacle, configured to rotatably receive the cannulated set screw and comprising a receptacle channel;
    a cable, positionable in the screw channel of the cannulated set screw and in the receptacle channel of the cannulated receptacle when the cannulated set screw is received by the cannulated receptacle; and
    a cannulated tool configured to prevent rotation of the cannulated receptacle, to tension the cable, and to rotatably drive the cannulated set screw into the cannulated receptacle while the cannulated tool prevents rotation of the cannulated receptacle and tensions the cable;
    wherein:
        the cannulated tool has a central axis;
        the screw driving feature comprises a drive gear and a driven gear;
        the driven gear is rotatable about a first axis that is concentric with the central axis of the cannulated tool and concentric with a central axis of the cannulated receptacle when the cannulated tool rotatably drives the cannulated set screw into the cannulated receptacle; and
        the drive gear is rotatable about a second axis that is oblique to the central axis of the cannulated tool and oblique to the central axis of the cannulated receptacle when the cannulated tool rotatably drives the cannulated set screw into the cannulated receptacle.

11. The system according to claim 10, wherein the cannulated tool comprises:
    a body;
    a screw driving feature, rotatable relative to the body and configured to co-rotatably engage the cannulated set screw;
    an anti-rotation feature, rotatable relative to the screw driving feature and configured to fixedly engage the cannulated receptacle; and
    a cable tensioning feature, configured to tension the cable when passed through the cannulated tool.

12. The system according to claim 11, wherein:
    the cable tensioning feature comprises an actuator that is rotatable to tension the cable; and
    the cannulated tool further comprises a tension quick-release mechanism that is selectively operable to release all tension in the cable independently of the cable tensioning feature.

13. The system according to claim 10, further comprising a driving tool configured to rotatably engage the drive gear, wherein a rotational axis of the driving tool is concentric with the second axis and oblique to the first axis when rotatably engaged with the drive gear.

14. A method of crimping a cable, the method comprising:
- positioning a cable in a screw channel of a cannulated set screw;
- positioning the cable in a receptacle channel of a cannulated receptacle;
- with the cable positioned in the screw channel and the receptacle channel, receiving the cannulated set screw in the cannulated receptacle;
- passing the cable through a cannulated tool having a central axis;
- tensioning the cable with a cable tensioning feature of the cannulated tool by rotating an actuator of the cannulated tool;
- engaging the cannulated receptacle with an anti-rotation feature of the cannulated tool; and
- after tensioning the cable and engaging the cannulated receptacle with the anti-rotation feature, rotating the cannulated set screw into engagement with the cannulated receptacle by rotating a drive gear of a screw driving feature of the cannulated tool, about a first axis that is oblique to the central axis of the cannulated tool, and rotating a driven gear of the screw driving feature of the cannulated tool, about a second axis that is concentric with the central axis of the cannulated tool, relative to the anti-rotation feature of the cannulated tool.

* * * * *